(12) United States Patent
 Ischiropoulos et al.

(10) Patent No.: US 10,590,063 B2
(45) Date of Patent: *Mar. 17, 2020

(54) COMPOSITIONS AND METHODS FOR THE TREATMENT OF FATTY ACID METABOLISM DISORDERS

(71) Applicant: The Children's Hospital of Philadelphia, Philadelphia, PA (US)

(72) Inventors: Harry Ischiropoulos, Media, PA (US); Paschalis-Thomas Doulias, Ioannina (GR)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/774,129

(22) PCT Filed: Nov. 7, 2016

(86) PCT No.: PCT/US2016/060785
§ 371 (c)(1),
(2) Date: May 7, 2018

(87) PCT Pub. No.: WO2017/079721
PCT Pub. Date: May 11, 2017

(65) Prior Publication Data
US 2018/0297931 A1     Oct. 18, 2018

Related U.S. Application Data

(60) Provisional application No. 62/251,860, filed on Nov. 6, 2015.

(51) Int. Cl.
*C07C 203/04*    (2006.01)
*A61K 31/195*    (2006.01)
(Continued)

(52) U.S. Cl.
CPC .......... *C07C 203/04* (2013.01); *A61K 31/192* (2013.01); *A61K 31/195* (2013.01);
(Continued)

(58) Field of Classification Search
CPC ....... C07C 203/04; A61P 3/06; A61K 31/192; A61K 31/215; A61K 31/195; G01N 2800/04

See application file for complete search history.

(56) References Cited

U.S. PATENT DOCUMENTS

| 10,137,103 B2 | 11/2018 | Ischiropoulos et al. |
| 2003/0199529 A1 | 10/2003 | Garvey et al. |

(Continued)

FOREIGN PATENT DOCUMENTS

| WO | 94/16740 A1 | 8/1994 |
| WO | 00/045649 A1 | 8/2000 |

(Continued)

OTHER PUBLICATIONS

Zolkipli et al. (PLoS ONE, 2011, vol. 6, Iss.4, el 7534, pp. 1-10) (Year: 2011).*

(Continued)

*Primary Examiner* — Angela C Brown-Pettigrew
(74) *Attorney, Agent, or Firm* — Robert C. Netter, Jr.; Dann, Dorfman, Herrell & Skillman

(57) ABSTRACT

Compositions and methods for inhibiting, treating, and/or preventing fatty acid metabolism disorders, particularly fatty acid oxidation disorders, in a subject are provided.

14 Claims, 16 Drawing Sheets

Specification includes a Sequence Listing.

(51) Int. Cl.
| | |
|---|---|
| A61K 31/215 | (2006.01) |
| A61K 31/23 | (2006.01) |
| A61K 31/192 | (2006.01) |
| A61K 31/198 | (2006.01) |
| A61K 45/06 | (2006.01) |
| G01N 33/68 | (2006.01) |
| A61P 3/06 | (2006.01) |
| A61K 31/225 | (2006.01) |

(52) U.S. Cl.
CPC .......... *A61K 31/198* (2013.01); *A61K 31/215* (2013.01); *A61K 31/23* (2013.01); *A61K 45/06* (2013.01); *A61P 3/06* (2018.01); *G01N 33/6893* (2013.01); *A61K 31/225* (2013.01); *A61K 2300/00* (2013.01); *G01N 2800/04* (2013.01)

(56) References Cited

U.S. PATENT DOCUMENTS

| | | | |
|---|---|---|---|
| 2009/0131342 | A1 | 5/2009 | Ellis |
| 2010/0062059 | A1 | 3/2010 | Ganzarolli De Oliveira |
| 2010/0069309 | A1 | 3/2010 | Gage |
| 2011/0077303 | A1 | 3/2011 | Sekhar |
| 2011/0092594 | A1 | 4/2011 | Yang |
| 2011/0105458 | A1 | 5/2011 | Branchaud |
| 2013/0012538 | A1 | 1/2013 | Uesugi et al. |
| 2013/0296424 | A1 | 11/2013 | Roe |
| 2016/0166525 | A1 | 6/2016 | Ischiropoulos et al. |

FOREIGN PATENT DOCUMENTS

| | | | |
|---|---|---|---|
| WO | 03/015605 | A2 | 2/2003 |
| WO | 2004/103307 | A2 | 12/2004 |
| WO | 2007/121545 | A1 | 11/2007 |
| WO | 2015/017383 | A2 | 2/2015 |

OTHER PUBLICATIONS

Clinical Trials (https://clinicaltrials.gov/ct2/history/NCT01379625?V_4=View#StudyPageTop, accessed Sep. 2, 2018, published Feb. 1, 2013) (Year: 2013).*

Andresen et al (Am. J. Hum. Genet. 64:479-494, 1999) (Year: 1999).*

Tenopoulou et al (The Journal of Biological Chemistry vol. 290, No. 16, pp. 10486-10494, Apr. 17, 2015) (Year: 2015).*

Doulias, P-T, et al., "Nitric Oxide Regulates Mitochondrial Fatty Acid Metabolism through Reversible Protein S-Nitrosylation," Sci. Signal. (2013) 6(256):rs1.

Rui-Qiong, M., et al., "Inhibition of Nitric Oxide Synthase Lowers Fatty Acid Oxidation in Preeclampsia-like Mice at Early Gestational Stage," Chi. Med. J. (2011) 24(19): 3141-3147.

Anderson, B.S., et al., "Clear Correlation of Genotype with Disease Phenotype in Very-Long-Chain Acyl-CoA Dehydrogenase Deficiency," Am. J. Hum. Genet. (1999) 64:479-494.

Gobin-Limballe, S., et al., "Genetic Basis for Correction of Very-Long-Chain Acyl-Coenzyme A Dehydrogenase Deficiency by Bezafibrate in Patient Fibroblasts: Toward a Genotype-Based Therapy," Am. J. Hum. Genet. (2007) 81:1133-1143.

Raju, K., et al., "Strategies and Tools to Explore Protein S-Nitrosylation," Biochim. Biophys. Acta (2012) 1820(6): 684-688.

Doulias, P-T, et al., "Structural Profiling of Endogenous S-nitrosocysteine Residues Reveals Unique Features that Accommodate Diverse Mechanisms for Protein S-nitrosylation," Proc. Natl. Acad. Sci. (2010) 107(39):16958-16963.

Kornberg, M.D., et al., "GAPDH Mediates Nitrosylation of Nuclear Proteins," Nat. Cell Biol. (2010) 12(11):1094-1100.

Deoliveira, C.P.M.S., et al., "Prevention and Reversion of Nonalcoholic Steatohepatitis in OB/OB Mice by S-Nitroso-N-Acetylcysteine Treatment," J. Amer. Coll. Nutr. (2008) 27(2):299-305.

Rinaldo, P., et al., "Fatty Acid Oxidation Disorders" Annu. Rev. Physiol. (2002) 64:477-502.

Zolkipli, Z., et al., "Vulnerability to oxidative stress in vitro in pathophysiology of mitochondrial short-chain acyl-CoA dehydrogenase deficiency: response to antioxidants" PLoS One (2011) 6(4):e17534.

Tenopoulou, M., et al., "Strategies for Correcting Very Long Chain Acyl-CoA Dehydrogenase Deficiency" J. Biol. Chem. (2015) 290(16):10486-10494.

Zamani, P., et al., "Effect of inorganic nitrate on exercise capacity in heart failure with preserved ejection fraction" Circulation (2015) 131:371-380.

Gould, N.S., et al., "Site-specific proteomic mapping identifies selectively modified regulatory cysteine residues in functionally distinct protein networks" Chem. Biol. (2015) 22:965-75.

Lange, K., et al., "NO donors. Part 18: Bioactive metabolites of GTN and PETN—Synthesis and vasorelaxant properties" Bioorg. Med. Chem. Lett. (2009) 19:3141-3144.

Mattson, F.H., et al., "Synthesis and Properties of Glycerides" J. Lipid Res. (1962) 3(3):281-296.

Goetzman, E.S., "Modeling Disorders of Fatty Acid Metabolism in the Mouse" in "Progress in Molecular Biology and Translational Science", Elsevier, Netherlands, 2011, vol. 100, pp. 389-417.

* cited by examiner

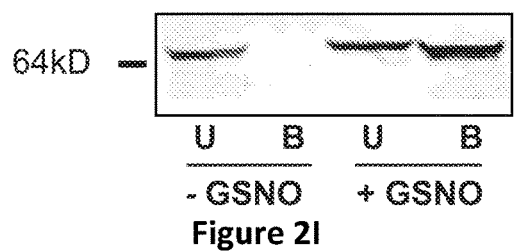
Figure 2I
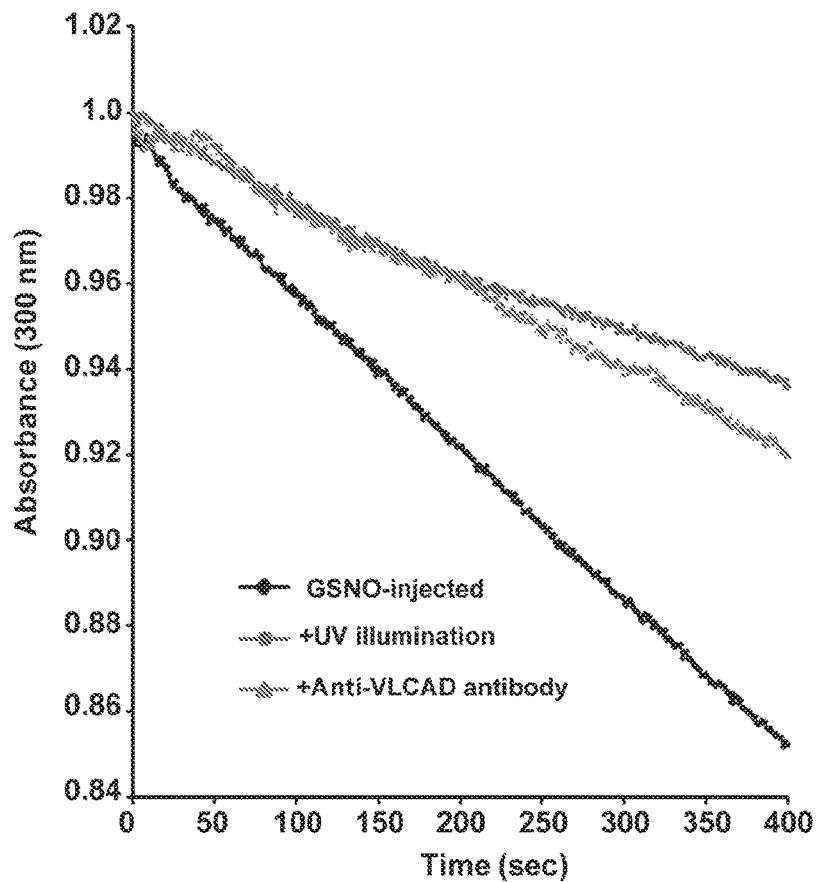
Figure 2J
| [Palmitoyl-CoA] mM | 0.015 | 0.03 | 0.06 | 0.125 | 0.25 |
|---|---|---|---|---|---|
| WT | 0.24 ± 0.05 | 0.33 ± 0.08 | 0.6 ± 0.02 | 1.41 ± 0.4 | 1.19 ± 0.1 |
| PBS injected | 0.08 ± 0.03 * | 0.13 ± 0.03 * | 0.17 ± 0.02 * | 0.32 ± 0.05 * | 0.58 ± 0.15 * |
| GSNO injected | 0.23 ± 0.06 | 0.43 ± 0.08 | 0.59 ± 0.14 | 0.84 ± 0.21 | 1.22 ± 0.26 |
| [Palmitoyl-CoA] mM | 0.5 | 0.75 | 1 | 2 |
|---|---|---|---|---|
| WT | 1.65 ± 0.32 | 1.39 ± 0.15 | 1.37 ± 0.27 | NA |
| PBS injected | 0.64 ± 0.16 * | 1.22 ± 0.47 | 1.47 ± 0.26 | 1.42 ± 0.1 |
| GSNO injected | 1.47 ± 0.32 | 1.45 ± 0.43 | 1.54 ± 0.34 | NA |
Figure 2K

SEQUENCE LISTING

<160> NUMBER OF SEQ ID NOS: 4

<210> SEQ ID NO 1
<211> LENGTH: 39
<212> TYPE: DNA
<213> ORGANISM: Artificial Sequence

```
<220> FEATURE:
<223> OTHER INFORMATION: Primer

<400> SEQUENCE: 1
tcagccatac ccagccccgc tggaaaatat tacactctc                           39

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
gagagtgtaa tattttccag cggggctggg tatggctga                           39

<210> SEQ ID NO 3
<211> LENGTH: 18
<212> TYPE: PRT
<213> ORGANISM: Artificial Sequence
<220> FEATURE:
<223> OTHER INFORMATION: tryptic peptide

<400> SEQUENCE: 3

Ser Ser Ala Ile Pro Ser Pro Cys Gly Lys Tyr Tyr Thr Leu Asn Gly
1               5                   10                  15

Ser Lys

<210> SEQ ID NO 4
<211> LENGTH: 17
<212> TYPE: PRT
<213> ORGANISM: Artificial Sequence
<220> FEATURE:
<223> OTHER INFORMATION: peptide

<400> SEQUENCE: 4

Thr Ser Ala Val Pro Ser Cys Gly Lys Tyr Tyr Thr Leu Asn Gly Ser
1               5                   10                  15

Lys
```

COMPOSITIONS AND METHODS FOR THE TREATMENT OF FATTY ACID METABOLISM DISORDERS

This application is a § 371 application of PCT/US2016/060785, filed Nov. 7, 2016, which claims priority under 35 U.S.C. § 119(e) to U.S. Provisional Patent Application No. 62/251,860, filed Nov. 6, 2015. The foregoing applications are incorporated by reference herein.

FIELD OF THE INVENTION

The present invention relates to compositions and methods for treating, preventing, and/or inhibiting fatty acid oxidation disorders.

BACKGROUND OF THE INVENTION

Several publications and patent documents are cited throughout the specification in order to describe the state of the art to which this invention pertains. Each of these citations is incorporated herein by reference as though set forth in full.

Very long chain acyl CoA dehydrogenase (VLCAD) is one of the four acyl-CoA dehydrogenases. VLCAD is a homodimeric mitochondrial protein that catalyzes the first step in the β-oxidation of fatty acids. VLCAD has activity mainly toward CoA-esters of fatty acids with 16-24 carbons in length and is responsible for more that 80% of palmitoyl-CoA dehydrogenation in human tissues and mammalian organs and cells, indicating that it is the major contributor in mitochondrial fatty acid oxidation.

VLCAD deficiency is an autosomal recessive genetic disorder first identified in 1993 and now considered as the second most common mitochondrial β-oxidation disorder. The associated disease presents with three main phenotypes. The most severe form of VLCAD deficiency presents with neonatal cardiomyopathy and hepatic failure and is generally fatal in the first year of life. An infantile phenotype typically presents during early childhood with hypoketotic hypoglycemia and hepatomegaly without cardiomyopathy. The mildest phenotype is associated with later onset episodic myopathic form with intermittent rhabdomyolysis, muscle cramps and/or pain and exercise intolerance. To date, more than 100 pathologic mutations are known including null (typically associated with the most severe form of the disease) as well missense mutations that occur throughout the VLCAD protein and are associated with the milder forms of the disease. Missense mutations result in reduced enzymatic activity and/or reduced stability of the protein leading to lower steady state levels of acyl-CoA activity in mitochondria. Upon diagnosis of VLCAD disease the effort is placed on the prevention of its manifestations. Individuals are typically placed on a low-fat formula with supplemental calories provided through medium-chain triglycerides. Superior methods of treatment and prevention are needed.

SUMMARY OF THE INVENTION

In accordance with the instant invention, methods for treating, inhibiting, and/or preventing a fatty acid metabolism disorder, particularly a fatty acid oxidation disorder, are provided. The method comprises administering at least one nitrosylating agent, particularly an S-nitrosylating agent, to the subject. In a particular embodiment, the fatty acid oxidation disorder is very long-chain acyl-coenzyme A dehydrogenase deficiency (VLCADD). In a particular embodiment, the S-nitrosylating agent is S-nitroso-N-acetyl-cysteine (SNO-NAC). In a particular embodiment, the S-nitrosylating agent comprises a nitrated fatty acid or triglyceride. In a particular embodiment, the S-nitrosylating agent is mononitrated-diheptanoin. The methods may further comprise administering at least one other therapeutic agent for the treatment of the fatty acid metabolism disorder, such as triheptanoin or bezafibrate. The methods may also comprise diagnosing a fatty acid oxidation disorder in the subject prior to administration of the S-nitrosylating agent.

In accordance with another aspect of the instant invention, compositions for treating, inhibiting, and/or preventing a fatty acid metabolism disorder, particularly a fatty acid oxidation disorder, are provided. In a particular embodiment, the composition comprises at least one S-nitrosylating agent, at least one pharmaceutically acceptable carrier, and, optionally, at least one other therapeutic agent for the treatment of a fatty acid metabolism disorder. In a particular embodiment, the composition comprises a nitrated fatty acid or triglyceride, particularly mononitrated-diheptanoin.

BRIEF DESCRIPTION OF THE DRAWING

FIGS. 1A and 1B provide representative mass spectrometry (MS) spectra of doubly-charged sulfonic acid-containing tryptic peptide, $Ser^{231}$-Ser-Ala-Ile-Pro-Ser-Pro-$Cys^{238}$-Gly-Lys-Tyr-Tyr-Thr-Leu-Asn-Gly-Ser-$Lys^{248}$ (SEQ ID NO: 3; monoisotopic m/z=960.9539 and 960.9561) from very long chain specific acyl dehydrogenase (VLCAD) acquired in liver homogenates from ob/ob GSNO injected mice and $eNOS^{-/-}$ liver after ex vivo treatment with GSNO (N=3 biological replicates). Spectra for the same peptide were acquired in wild-type mouse liver. FIGS. 1C and 1D show that MS/MS spectra confirmed the sequence and site of sulfonic acid containing peptide from VLCAD identified in ob/ob mouse liver injected with GSNO and $eNOS^{-/-}$ liver after ex vivo treatment with GSNO (N=3 biological replicates). SEQ ID NO: 3 is shown in FIGS. 1C and 1D.

as compared to PBS-treated ob/ob mice (top). Images are representative of four different mouse livers examined. The scale bar corresponds to 15 μm for left and to 7.5 μm for right. FIG. 2I shows Western blot analysis of VLCAD fractions that did not bind (U=unmodified VLCAD) and bound to organomercury (B=S-nitrosylated VLCAD) from eNOS$^{-/-}$ mouse liver homogenates and eNOS$^{-/-}$ mouse liver homogenates treated with GSNO. The absence of VLCAD from the bound fraction of the untreated homogenate indicated that the protein was not S-nitrosylated in eNOS$^{-/-}$ liver. Ex vivo treatment with GSNO resulted in S-nitrosylation of a fraction of the protein as it was indicated by the immunoreactivity in the bound fraction of the treated homogenate. This experiment was repeated twice more with similar results. FIG. 2J shows typical tracings of VLCAD acyl-dehydrogenase activity using 150 μM ferricenium hexafluorophosphate as electron acceptor. The activity was measured in liver homogenates from GSNO-injected ob/ob mice after the addition of 0.125 mM palmitoyl-CoA. The specificity of the assay for measuring VLCAD activity was confirmed by the abolishment of ferricenium reduction in the presence of anti-VLCAD antibodies. The effect of S-nitrosylation on VLCAD activity was confirmed by the loss of enzymatic activity after UV-photolysis of liver lysate. This experiment was repeated once more in another biological replicate with identical results. FIG. 2K presents the initial velocity ($V_O$) measured as a function of palmitoyl-CoA concentration in liver homogenates from three groups of mice. *p<0.05 by t-test. N=3 biological replicates.

FIG. 7A: Serum levels of nitrogen oxides. FIG. 7B: Heart levels of nitrogen oxides. FIG. 7C: mFAO rate. FIG. 7D: VLCAD specific activity. In parentheses is indicated the fraction of S-nitrosylated VLCAD. ND indicates Not Detected. * denotes statistical difference of p<0.01 as compared to NaNO$_2$-treated and wild type mice (N=3). ** denotes statistical difference of p<0.05 between NaNO$_2$-treated and wild type mice (N=3).

DETAILED DESCRIPTION OF THE INVENTION

Figure 1A:
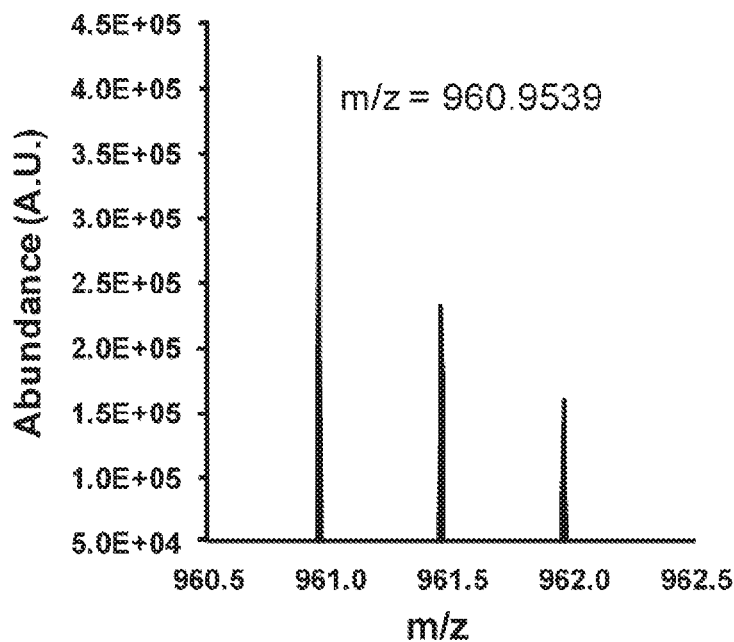
FIGS. 1A-1D show the identification of the S-nitrosylation site in VLCAD.

Mitochondrial fatty acid oxidation (mFAO) is the main metabolic process for energy production in the heart, skeletal muscle, and kidney under physiological conditions. mFAO is also an indispensable energy source during nutrient deprivation, exposure to cold, and exercise. Children with genetic deficiencies in mFAO experience cardiac, hepatic, and skeletal muscle dysfunction. Beyond the well-characterized genetic metabolic disorders, inefficient mFAO has been implicated in the pathogenesis of highly prevalent metabolic disorders such as non-alcoholic fatty liver disease (NAFLD) and type 2 diabetes. Herein, novel pharmacological approaches to enhance mFAO activity in vivo are provided. A pre-clinical mouse model with cardiac-specific very long chain acyl-CoA dehydrogenase (VLCAD) deficiency may be used to augment mFAO activity in order to avert metabolic decompensation and clinical phenotypes. Using well-characterized human fibroblast lines derived from subjects with clinically documented VLCAD deficiency, the efficacy of compounds in restoring mFAO can be tested. Therapeutic modalities will significantly impact the lives of children and adults with mFAO deficiencies as well as subjects with highly prevalent non-congenital metabolic disorders.

The primary pathway for the metabolism of long-chain fatty acids is mitochondrial fatty acid β-oxidation (mFAO). Cardiac muscle generates more than 50% of energy (ATP) required for normal cardiovascular function from mFAO. mFAO is also essential for ATP production in skeletal muscle, especially during exercise, and in the kidneys where tubular epithelial cells depend on mFAO as their energy source. Finally, the essential for life adaptive response to starvation or fasting relies primarily on liver mFAO activity. Fasting triggers the release of fatty acids stored as triglycerides in adipose tissue, transport, and uptake of fatty acids into the liver where oxidation by mFAO fuels the tricarboxylic acid (TCA) cycle and oxidative phosphorylation and stimulates synthesis and release of ketone bodies, (R)-3-hydroxybutyrate and acetoacetate. Ketone bodies are used as metabolic fuel by the brain and kidneys.

The biological importance of mFAO is highlighted by patients with inherited metabolic disorders caused by defects in the mFAO pathway/proteins. Patients with mFAO disorders typically exhibit intolerance to fasting, cold, and exercise, often presenting with hypoketotic hypoglycemia that may progress into life-threatening syndromes, as well as cardiac and skeletal muscle abnormalities.

mFAO is regulated by transcriptional mechanisms that control expression of the nearly 20 genes participating in mFAO as well as by post-transcriptional mechanisms. Post-transcriptional regulation of mFAO involves the allosteric inhibition of carnitine palmitoyltransferase-1 (CPT1) by malonyl-CoA which is generated by acetyl-CoA carboxylases (ACC1 and ACC2). CPT1 converts fatty acid-CoA species to acylcarnitines for transport into the mitochondria. Inside the mitochondria a four step cyclic enzymatic process shortens the long fatty acid acyl-CoA species by two carbons in each cycle, eventually producing acetyl-CoA and carbon dioxide. For example, complete oxidation of palmitoyl-CoA requires 7 cycles through the β-oxidation spiral to generate 8 acetyl-CoA molecules which are partitioned between the TCA cycle and production of secreted ketone bodies.

Recent evidence has indicated that key proteins in the mFAO pathway are regulated by post-translational modifications, phosphorylation, acetylation, and S-nitrosylation. Very long chain acyl-CoA dehydrogenase (VLCAD) is responsible for more than 80% of palmitoyl-CoA dehydrogenation in humans and is regulated by nitric oxide (NO). The discovery of NO as a signaling molecule in the cardiovascular system has prompted numerous studies, which indicate that defects in the synthesis and bioavailability of endothelial-derived NO are central to the pathogenesis of cardiovascular and metabolic disorders. Using innovative proteomic technologies, selective S-nitrosylation, a post-translational modification of cysteine residues by NO equivalents, has been determined to be an alternative but complimentary NO-mediated signaling pathway. The data establish that S-nitrosylation of enzymes in the mFAO pathway and specifically VLCAD are important regulators of fatty acid oxidation. In the mouse liver VLCAD protein is endogenously and selectively S-nitrosylated at cysteine 238. S-nitrosylation increases the catalytic efficiency of VLCAD by 29-fold.

In states of NO deficiency, such as in the endothelial nitric oxide synthase null (eNOS$^{-/-}$) or leptin null mice, VLCAD is not S-nitrosylated resulting in diminished mFAO rate as compared to wild type mice leading to a profound increase in liver triglycerides and eventually to hepatic steatosis. It is shown herein that the pharmacological delivery of NO equivalents via S-nitroso-glutathione (GSNO) or nitrite, restores S-nitrosylation and catalytic efficiency of VLCAD, improves overall mFAO, and reduces the pathological hepatic phenotypes.

Moreover, using a similar strategy, it is shown that pharmacological restoration of VLCAD S-nitrosylation improved VLCAD specific activity in the setting of VLCAD deficiency. Skin fibroblasts were obtained from individuals with clinically diagnosed VLCAD defect (mutations in the VLCAD gene: G185S/G294E, N122D/N122D, P89S/A536fsX550 and P91Q/G193R) were treated with S-nitroso-N-acetyl-cysteine (SNAC). All four subjects have residual VLCAD protein and activity. A substantial increase of mutant VLCAD specific activity upon treatment of fibroblasts with SNAC as well S-nitrosylation of VLCAD on cysteine 237 (238 in the mouse sequence a residue that is conserved among mammalian VLCADs) was documented. Furthermore, mFAO capacity and acylcarnitine levels were normalized in VLCAD-deficient cells treated with SNAC. Overall, these data demonstrate the utility of NO-based pharmacological interventions for correcting mFAO and mitigating clinical symptoms.

The NO-based pharmacology has a long history starting with nitroglycerin, to sildenafil and inhaled NO. The current pharmacological landscape includes the use of inorganic nitrate and nitrite to replenish NO in humans with various cardiovascular and metabolic disorders. Nitrite, a metabolite of endogenously produced NO, represents a storage pool of NO that can be activated by several pathways to produce bioactive NO. Several forms of nitrite (oral tablet, sustained-release tablet and inhaled) are considered safe and approved for clinical testing in humans. Other options include: (i) S-nitroso-glutathione (GSNO)—a physiological form of bioactive NO—or the precursor of GSNO, the tripeptide glutathione (GSH); (ii) S-nitroso-N-acetyl-cysteine (SNAC), which is similar to GSNO, or the precursor N-acetyl-cysteine. These two molecules can deliver bioactive NO but also execute selective transfer of NO equivalent to a reduced thiol of cysteine residues in proteins to restore protein S-nitrosylation (a function that classifies them as S-trans-nitrosylating agents).

As in the case of VLCAD, large scale proteomic work uncovered that the mouse proteome contains proteins with unique cysteine residues within evolutionary conserved protein segments and outside commonly annotated functional regions that are modified by S-nitrosylation. Critically, the data showed that S-nitrosylation is restricted within biologically related protein networks and prominently within metabolic pathways. This limited and restrictive biochemistry implies that restoration of protein S-nitrosylation can be achieved pharmacologically and pharmacophores that target S-nitrosylation of mFAO proteins in vivo can be used in the setting of disorders that are induced by inefficient metabolism of fatty acids. Herein, pediatric metabolic disorders are targeted since there are no apparent long term treatments. Specifically, VLCAD deficiency, which represents the second most common among the mFAO disorders, is targeted. Children with VLCAD deficiency (have residual protein and enzymatic activity) exhibit hypertrophic or dilated cardiomyopathy, pericardial effusion, and arrhythmias as well as hypotonia, hepatomegaly, and intermittent hypoglycemia. Children also present with significant muscle breakdown, exercise intolerance, and muscle pain. Upon clinical diagnosis, treatment includes low-fat formula with supplemental calories provided through medium-chain triglycerides. Beyond this standard of care approach, two clinical trials explored bezafibratesn and triheptanoin, an oil that is used as a food additive. Bezafibrates which are effective in most types of primary and secondary dyslipidemia have been also used in clinical trials for long-chain fatty acid oxidation disorders. However, in a randomized clinical trial, bezafibrate, as a solo agent, did not improve clinical symptoms or fatty acid oxidation during exercise in patients with VLCAD deficiency. Triheptanoin, a triglyceride with three heptanoin acids (a 7 carbon fatty acid) esterified to a glycerol backbone, is in Phase 2 trials targeting kids with long chain fatty acid oxidation defects and aiming to decrease muscle pain and to improve heart function (ClinicalTrials.gov Identifiers: NCT01379625 and NCT01886378). Triheptanoin fulfills two potential roles—it provides short chain fatty acids for mFAO and also serves an anaplerotic function by providing substrate (propionyl-CoA) for the production of pyruvate, which upon carboxylation produces oxaloacetate an intermediate substrate of the TCA cycle. Given these favorable functions of triheptanoin and the need to deliver NO equivalents, novel derivatives based on well-known esterification procedures are provided herein. The glycerol backbone esterified with 3 nitro groups produces nitroglycerin that replenishes bioactive NO and has life-saving vascular effects. Thus, as explained hereinbelow, mononitrated diheptanoin glycerol adducts were generated, primarily 1,3-diheptanoin-2-mononitrate. This molecule will retain the dual metabolic function of triheptanoin while furnishing NO equivalents inside the mitochondria that will selectively modify the residual VLCAD by S-nitrosylation augmenting the catalytic efficiency. Therefore these novel compounds will fulfill three important biological functions.

As seen hereinbelow, mFAO is enhanced in vivo through the increased availability of bioactive nitric oxide. This was accomplished by the use of sodium nitrite ($NaNO_2$), a molecule that is administrated safely to humans in current clinical trials. While the example hereinbelow used $eNOS^{-/-}$ mice, nitrite can also be administered orally to mice with cardiac-specific VLCAD (cVLCAD) deficiency. Cardiac specific deletion of VLCAD in mice leads to dilated cardiomyopathy and depressed left ventricle function by the age of six months in the absence of antecedent stress. At the same age heterozygous cVLCAD deficient ($cVLCAD^{+/-}$) mice show partly compromised cardiac function indicating gene dose and time dependent effects. $cVLCAD^{+/-}$ mice develop progressive cardiac pathology between the ages of 9 to 12 months. Therefore the $cVLCAD^{+/-}$ provide a suitable pre-clinical model since they develop a phenotype that can be monitored over time and have residual VLCAD activity that can be modulated pharmacologically. Using comprehensive mass spectrometry based technologies and functional assays, the long term effects of oral nitrite administration on cardiac, liver and homeostatic regulation of metabolism can be monitored. Cardiac anatomy and function using echocardiography and magnetic resonance imaging (MRI) technologies, respectively, may also be monitored. Cardiac energetics, energy expenditure, and activity may also be monitored using established biochemical methods and metabolic cages. Fatty acid oxidation rate, acyl carnitine and acyl-CoA species may also be quantified by LC-MS/MS. Enzymatic activities, protein expression levels and localization may also be assessed by established analytical and biochemical methods. Site-specific S-nitrosylation of VLCAD and the quantification of the fraction modified by S-nitrosylation may also be performed.

In a particular embodiment, male C57/BL6 and heterozygous cardiac-specific VLCAD deficient ($cVLCAD^{+/-}$) mice (in a C57/BL6 background) may be used. As explained above, $cVLCAD^{-/-}$ mice recapitulate major metabolic and phenotypic abnormalities present in humans with cardiac VLCAD deficiency. The $cVLCAD^{+/-}$ mice demonstrate signs of cardiac abnormalities (mild dilated cardiomyopathy and slightly depressed left ventricular function) at the age of six months. These functional deficits progress to a pathological phenotype (increased end-diastolic and end-systolic dimensions as well as reduced fractional shortening) by the age of 9-12 months.

In a particular embodiment of using the cVLCAD mice model for testing compounds, the $cVLCAD^{+/-}$ mice will be divided into two groups. One group will receive no treatment whereas the other will receive treatment (0.1 mM $NaNO_2$ in the drinking water. This concentration was selected based on preliminary data using endothelial nitric oxide synthase null mice ($eNOS^{-/-}$), a model of nitric oxide deficiency). Treatment (e.g., sodium nitrite treatment) may start at the age of 3 months when mice have no sign of cardiac dysfunction. To ascertain the cardiac phenotype, cardiac anatomy and left ventricular function may be evaluated monthly using non-invasive imaging techniques. Upon establishment of cardiac pathology in untreated $cVLCAD^{+/-}$ mice, the experiment may be terminated. Some and/or all of the following parameters may be quantified. (1) Metabolic monitoring: Mice may be housed individually in metabolic cages (e.g., by Columbus Instruments). One or more parameters may be monitored such as: body weight, food and water intake, activity, body temperature, oxygen consumption, and/or carbon dioxide production. The parameters may be monitored automatically (e.g., with the Oxymax/Comprehensive Lab Animal Monitoring System (CLAMS)). In a typical experiment, mice may be acclimated in the cage for 1 day and monitored for 24 hours (data is collected on 30-40 minute intervals). This monitoring may take place weekly upon the initiation of therapy. The respiratory quotient ($VCO_2/VO_2$), an indicator of energy source, may be calculated from the measurements of oxygen consumption and carbon dioxide production. Typically the respiratory quotient is 1.0 under fed conditions and respiratory quotient below 0.70 indicates that fat is the predominant fuel source. During the experiments activity, energy expenditure, respiratory exchange rate (RER), body temperature and/or heart rate may be monitored. (2) Assessment of cardiac anatomy and function. The cardiac anatomy may be determined using MRI technique in anesthetized mice with isoflurane. The left ventricle function and structure may be determined. Cardiac function may be evaluated by M-mode echocardiography. This technique has been successfully applied to monitor cardiac function in cVLCAD$^{-/-}$ mice. Quantification of ATP, ADP, AMP and NAD levels in heart homogenates may be performed using HPLC methodologies. (3) Quantification and profiling of lipids metabolites and acylcarnitine species. Plasma, heart and liver levels of triglycerides, free fatty acids and phospholipids may be quantified by established assays. Acyl carnitines, a clinically used biomarker for diagnosis, may be performed by LC-MS/MS using stable isotope-labeled internal standards. (4) Homeostasis Model Assessment (HOMA) Index. Plasma glucose and insulin may be measured in mice fasted overnight according to standard methodologies. (5) Evaluation of hepatic steatosis and liver injury. Hepatic MRI may be performed on unconscious mice according to established protocols. Liver histological staining with hemaotxylin, Biebrich Scarlet-fucshin and anilline blue (trichrome stain) may be performed to ascertain the phenotype or lack thereof. Liver injury may be assessed by measuring the levels of alanine aminotransferase (ALT) and aspartate aminotransferase (AST) in the plasma of mice. (6) Quantification of mFAO rate. For the quantification of mFAO rate, intact hearts and livers may be perfused with $U^{13}$-$C_{16}$ palmitate and the generation of [1,2]-$^{13}$C-acetyl-CoA may be monitored and quantified by LC-MS/MS according to established protocols. Analysis of VLCAD protein levels, enzymatic activity, kinetics and S-nitrosylation. (8) Functional interrogation of the heart and hepatic S-nitrosoproteomes upon completion of nitrite treatment. One potential consequence of delivering NaNO$_2$ for therapy will be the modification of additional cysteine residues on proteins. The S-nitrosocysteine proteome in tissue homogenates may be acquired and analyzed for gene ontology (GO) terms and functional classification. These analyses will determine whether specific molecular functions are enriched in NaNO$_2$-treated mice. Global proteomic identifications may also be performed and relative changes of protein expression in mice treated with NaNO$_2$ can be quantified.

Protein S-nitrosylation is a major nitric oxide-derived reversible posttranslational modification that regulates enzymatic activity, protein localization, and stability, and that also plays a role in nitric oxide-mediated signaling (Stamler et al. (2001) Cell 106:675-683; Hess et al. (2005) Nat. Rev. Mol. Cell Biol., 6:150-166; Benhar et al. (2008) Science 320:1050-1054; Jaffrey et al. (2001) Nat. Cell Biol., 3:193-197; Kornberg et al. (2010) Nat. Cell Biol., 12:1094-1100; Matsushita et al. (2003) Cell 115:139-150; Mitchell et al. (2005) Nat. Chem. Biol., 1:154-158; Cho et al. (2009) Science 324:102-105; Mannick et al. (2001) J. Cell Biol., 154:1111-1116). Although functional roles for S-nitrosylation have been documented for individual proteins, a global analysis of S-nitrosylation and the S-nitrosylation sites under physiological conditions in vivo remains limited. To this end, a mass spectrometry (MS)-based proteomic approach has been implemented which allows for the site-specific identification of S-nitrosocysteine residues in complex mixtures (Doulias et al. (2010) Proc. Natl. Acad. Sci., 107:16958-16963). The method is based on selective enrichment either of S-nitrosocysteine peptides or intact S-nitrosylated proteins with organomercury compounds. The peptides are released with performic acid, which oxidizes the cysteine to sulfonic acid, enabling precise detection of the modified peptides by MS. Alternatively, proteins can be eluted intact and probed with antibodies against specific proteins, enabling quantification of the modified protein molecules. To ensure specificity of detection, negative controls are generated by pretreatment of samples with ultraviolet (UV) light, which eliminates S-nitrosocysteine, and analyzed under the same conditions (Doulias et al. (2010) Proc. Natl. Acad. Sci., 107:16958-16963). These methodologies were used to identify endogenous S-nitrosylated proteins in six wild-type mouse organs, as well as in the same tissues from mice lacking the endothelial nitric oxide synthase (eNOS). A global discovery of the S-nitrosocysteine proteome in mice reveals potential functional regulation of core biochemical pathways by S-nitrosylation and the changes in this proteome in the absence of one of the major enzymatic sources of nitric oxide. Indeed, selective S-nitrosylation of enzymes participating in glycolysis, gluconeogenesis, tricarboxylic acid cycle, and oxidative phosphorylation has been found, indicating that this post-translational modification regulates metabolism and mitochondrial bioenergetics. S-nitrosylation of the murine liver enzyme very long chain acyl-coenzyme A (CoA) dehydrogenase (VLCAD) at Cys$^{238}$, which was absent in mice lacking endothelial nitric oxide synthase, improved its catalytic efficiency. Moreover, the administration of an S-nitrosylating agent to cells with a mutant VLCAD resulted in increased enzymatic activity. These data implicate protein S-nitrosylation in the regulation of β-oxidation of fatty acids in mitochondria.

The instant invention encompasses methods of inhibiting, treating, and/or preventing a fatty acid metabolism disorder. In a particular embodiment, the fatty acid metabolism disorder is a fatty acid oxidation disorder/deficiency (e.g., a mFAO disorder/deficiency). Fatty acid oxidation disorders include, without limitation, very long-chain acyl-coenzyme A dehydrogenase deficiency (VLCADD; e.g., 16-24 carbons), long-chain acyl-coenzyme A dehydrogenase deficiency (LCADD; e.g., 12-18 carbons), long-chain 3-hydroxyacyl-coenzyme A dehydrogenase deficiency (LCHADD), medium-chain acyl-CoA dehydrogenase deficiency (MCADD; e.g., 6-12 carbons), short chain acyl-CoA dehydrogenase deficiency (SCADD; e.g., 4-6 carbons), medium/short chain L-3-hydroxyacyl-CoA dehydrogenase deficiency (M/SCHADD), multiple acyl-CoA dehydrogenase deficiency (MADD), mitochondrial trifunctional protein deficiency, short chain 3-ketoacyl-CoA thiolase deficiency (SKATD), medium chain 3-ketoacyl-CoA thiolase deficiency (MCKATD), 2,4-dienoyl-CoA reductase deficiency, and glutaric acidemia type II (GA-II). In a particular embodiment, the fatty acid oxidation disorder is VLCADD.

The methods of the instant invention comprise administering at least one nitrosylating agent, particularly an S-nitrosylating agent, to a subject. As used herein the term "nitrosylation" refers to the addition of nitric oxide (NO) to a polypeptide, particularly at a thiol group (SH), oxygen, carbon or nitrogen. The term "S-nitrosylation" refers to the addition of a nitric oxide moiety to a thiol group, thereby forming an S-nitrosothiol (SNO). An "S-nitrosylating agent" refers to a compound that transfers a nitric oxide group to the thiol of a polypeptide to form an S-nitrosothiol. Examples of S-nitrosylating agents are provided in Feelisch, J., Stamler, J. S. (1996) Donors of Nitrogen Oxides. Feelisch, M.

Stamler, J. S. eds. Methods in Nitric Oxide Research, John Wiley & Sons, Ltd. Chichester, UK. S-nitrosylating agents include, without limitation, S-nitrosylating agents that directly nitrosylate (e.g., GSNO), precursor agents that are modified in vivo to S-nitrosylating agents (e.g., N-acetyl cysteine (NAC)), and nitric oxide generators that produce nitrosylators (e.g., nitrite plus GSH or NAC), as well as esters and/or salts thereof. S-nitrosylating agents include, without limitation, acidic nitrite, nitrosyl chloride, alkyl nitrate (e.g., ethyl nitrite), amyl nitrite, glutathione (GSH), glutathione oligomer, S-nitrosoglutathione (GSNO), S-nitrosocysteinyl glycine, S-nitrosocysteine, N-acetyl cysteine, S-nitroso-N-acetyl cysteine, nitroglycerine, nitroprusside, nitric oxide, S-nitrosohemoglobin, S-nitrosoalbumin, 5-nitroso-N-acetylpenicillamine, S-nitroso-gamma-methyl-L-homocysteine, 5-nitroso-L-homocysteine, S-nitroso-gamma-thio-L-leucine, S-nitroso-delta-thio-L-leucine, and S-nitrosoalbumin, as well as pharmaceutically acceptable salts thereof. In a particular embodiment, the S-nitrosylating agent is S-nitroso-N-acetyl-cysteine (SNO-NAC). The methods of the instant invention may further comprise the administration (sequentially and/or simultaneously) of at least one other therapeutic for the treatment of the fatty acid metabolism disorder. For example, the methods may further comprise administering triheptanoin and/or bezafibrate. The subject may also be administered a diet that reduces or eliminates the presence of problematic fatty acids (e.g., fatty acids that are substrates for the deficient enzyme), e.g., fatty acids with 12 or fewer carbons or fatty acids with more than 12 or 16 carbons (e.g., for VLCADD).

Figure 8:
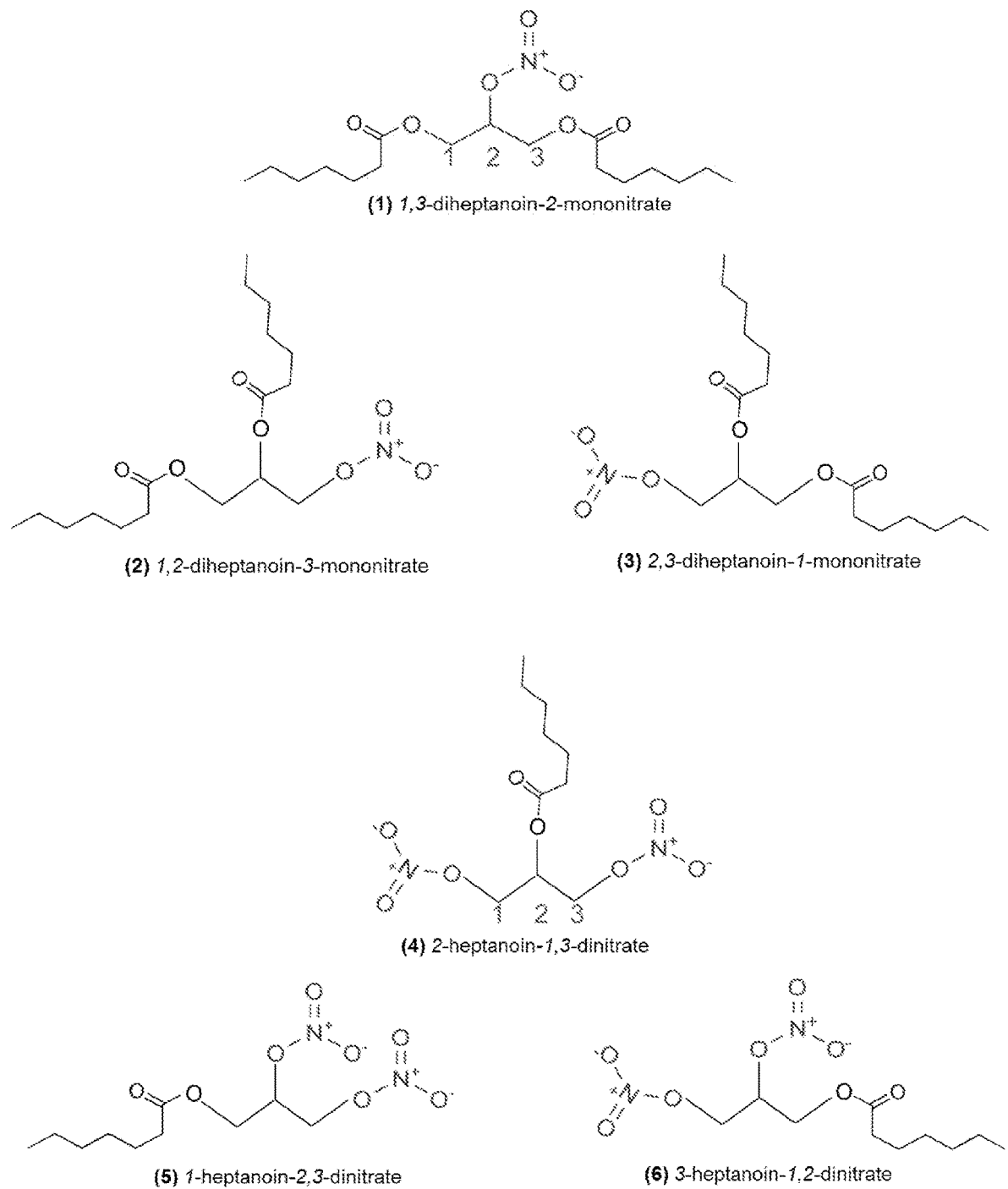
FIG. 8 provides chemical structures of certain monoheptanoin-dinitrates and diheptanoin-mononitrates.

In a particular embodiment, the S-nitrosylating agent is/comprises a nitrated fatty acid. The S-nitrosylating agent may be mononitrated, dinitrated, trinitrated, or more. In a particular embodiment, the fatty acid comprises fewer than 12 carbons, particularly fewer than 10 carbons. In a particular embodiment, the fatty acid comprises at least 7 carbons. In a particular embodiment, the fatty acid comprises about 7 to about 11 carbons, particularly about 7 to about 9 carbons. The S-nitrosylating agent may comprise one fatty acid, two fatty acids, three fatty acids, or more. In a particular embodiment, the S-nitrosylating agent is a triglyceride wherein one or two of the fatty acids are replaced by an NO equivalent (e.g., nitrate, nitroso, nitro, etc.). In a particular embodiment, the nitrate can be added to the glycerol backbone at any of the three positions. In a particular embodiment, the S-nitrosylating agent comprises heptanoin, particularly diheptanoin or monoheptanoin. In a particular embodiment, the S-nitrosylating agent comprises diheptanoin. Examples of heptanoin containing compounds include, without limitation: 1,3-diheptanoin-2-mononitrate; 1,2-diheptanoin-3-mononitrate; 2,3-diheptanoin-1-mononitrate; 1,3-dinitrate-2-heptanoin; 1,2-dinitrate-3-heptanoin; and 2,3-dinitrate-1-heptanoin. In a particular embodiment, the S-nitrosylating agent is mononitrated-diheptanoin (diheptanoin mononitrate). In a particular embodiment, the S-nitrosylating agent is dinitrate hepatnoin (e.g., 1,3, dinitrate-2-heptanoin). FIG. 8 provides chemical structures of certain of these compounds.

Diheptanoin mononitrate can be synthesized from glyceryl-2-mononitrate and heptanoic acid. Glyceryl-2-mononitrate (glycerol with a nitro group in the carbon 2 position) is a viscous, hygroscopic liquid which is soluble in water, alcohol and ether. The esterification of the glyceryl-2-mononitrate with heptanoic acid produces 1,3-diheptanoin, 2-mononitrate. Glyceryl-2-mononitrate may be placed in a reaction flask with heptanoic acid in a 1:1.5 molar ratio in the presence of basic catalyst. The mixture may then be heated above its melting point for 2 hours. The temperature may then be decreased slowly so that the preferential crystallization of the 1,3-diglyceride of the high molecular weight fatty acid results in directed interesterification to this product. The catalyst may then be inactivated with acetic acid and the 1,3-diglycerides recovered by filtration and purified by crystallization. 2-mononitrate-1,3-diglycerides may also be formed by heating glyceryl-2-mononitrate with heptanoic acid in the presence of a quaternary ammonium salt. Both approaches are relative mild reactions that result in high yields and great purity of the 1,3-diglyceride. Typical yields are >98%. Purity may be evaluated by HPLC-mass spectrometry. The product may be tested in human fibroblasts comprising mutations in the VLCAD gene (see Example 2).

The S-nitrosylating agent may be delivered to the subject as a composition with at least one pharmaceutically acceptable carrier. In a particular embodiment, the composition further comprises at least one other therapeutic agent for the treatment of the fatty acid metabolism disorder, as described above.

As stated hereinabove, the instant invention encompasses methods of inhibiting, treating, and/or preventing a fatty acid metabolism disorder in a subject. The method may further comprise diagnosing a fatty acid metabolism disorder in the subject prior to administration of the therapeutic agents of the instant invention. More specifically, the method may further comprise determining whether the subject has deficient VLCAD enzymatic activity compared to healthy subjects. Methods of determining VLCAD activity are known in the art. For example, a biological sample may be obtained from the subject and a VLCAD enzymatic assay may be performed (e.g., an acyl-CoA dehydrogenase assay using ferricenium ion) and compared to a standard value (e.g., from healthy subjects and/or a subject with the fatty acid metabolism disorder) or directly compared to a biological sample from a healthy subject and/or a subject with the fatty acid metabolism disorder. Alternatively (or additionally), VLCAD activity may be measured by determining whether the subject has a missense mutation in VLCAD (e.g., those presented in Table 1) and/or null mutation (e.g., resulting in a VLCAD with deficient activity). VLCAD mutations are also provided in Gobin-Limballe et al. (Am. J. Hum. Genet. (2007) 81:1133-1143 (see, e.g., FIG. 1 and Table 1)) and Andresen et al. (Am. J. Hum. Genet. (1999) 64:479-494 (see, e.g., Table 2)). Each of these references is incorporated herein by reference as though set forth in full. Methods of detecting VLCAD mutations are known in the art. For example, a biological sample may be obtained from the subject and the VLCAD gene may be sequenced or the nucleic acids from the biological sample may be contacted with one or more probes (e.g., specific for wild-type or a mutant). Alternatively, the presence of mutant VLCAD may be detected through the use of antibodies immunologically specific for wild-type or mutant VLCAD. When the subject is determined to have deficient VLCAD enzymatic activity and/or determined to carry a missense or null mutation, the subject may then be treated by the methods of the instant invention.

The compositions of the present invention can be administered by any suitable route, for example, by injection (e.g., for local, direct, or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered orally and/or intraperitoneally. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention (see, e.g., Remington's Pharmaceutical Sciences and Remington: The Science and Practice of Pharmacy). The pharmaceutical composition of the present invention can be prepared, for example, in liquid form, or can be in dried powder form (e.g., lyophilized for later reconstitution).

The therapeutic agents described herein will generally be administered to a subject/patient as a pharmaceutical preparation. The term "patient" as used herein refers to human or animal subjects. The compositions of the instant invention may be employed therapeutically or prophylactically, under the guidance of a physician.

The compositions comprising the agent of the instant invention may be conveniently formulated for administration with any pharmaceutically acceptable carrier(s). The concentration of agent in the chosen medium may be varied and the medium may be chosen based on the desired route of administration of the pharmaceutical preparation. Except insofar as any conventional media or agent is incompatible with the agent to be administered, its use in the pharmaceutical preparation is contemplated.

The dose and dosage regimen of the agent according to the invention that is suitable for administration to a particular patient may be determined by a physician considering the patient's age, sex, weight, general medical condition, and the specific condition for which the agent is being administered to be treated or prevented and the severity thereof. The physician may also take into account the route of administration, the pharmaceutical carrier, and the agent's biological activity. Selection of a suitable pharmaceutical preparation will also depend upon the mode of administration chosen.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment or prevention therapy. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation or prevention of a particular condition may be determined by dosage concentration curve calculations, as known in the art.

The pharmaceutical preparation comprising the agent may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Toxicity and efficacy (e.g., therapeutic, preventative) of the particular formulas described herein can be determined by standard pharmaceutical procedures such as, without limitation, in vitro, in cell cultures, ex vivo, or on experimental animals. The data obtained from these studies can be used in formulating a range of dosage for use in human. The dosage may vary depending upon form and route of administration. Dosage amount and interval may be adjusted individually to levels of the active ingredient which are sufficient to deliver a therapeutically or prophylactically effective amount.

Definitions

The following definitions are provided to facilitate an understanding of the present invention:

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween® 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions may be employed as carriers, particularly for injectable solutions. Suitable pharmaceutical carriers are described in "Remington's Pharmaceutical Sciences" by E.W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., fatty acid oxidation disorder) resulting in a decrease in the probability that the subject will develop the condition.

A "therapeutically effective amount" of a compound or a pharmaceutical composition refers to an amount effective to prevent, inhibit, or treat a particular disorder or disease and/or the symptoms thereof. For example, "therapeutically effective amount" may refer to an amount sufficient to modulate fatty acid oxidation in a subject.

As used herein, the term "subject" refers to an animal, particularly a mammal, particularly a human.

As used herein, a "biological sample" refers to a sample of biological material obtained from a subject, particularly a human subject, including a tissue, a tissue sample, cell(s), and a biological fluid (e.g., blood).

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The following examples are provided to illustrate various embodiments of the present invention. They are not intended to limit the invention in any way.

Example 1

Materials and Methods
Chemicals and Reagents

Palmitoyl-CoA lithium salt and ferricenium hexafluorophosphate were obtained from Sigma-Aldrich. Mouse monoclonal antibodies against FLAG®, glyceraldehyde-3-phosphate dehydrogenase, and cytochrome c oxidase subunit I were from Stratagene and Abcam, respectively. Rabbit and goat (G-16 clone) polyclonal antibodies against VLCAD were obtained from GeneTex and Santa Cruz Biotechnology, respectively. All chemicals and reagents used were of analytical grade.

Isolation of Mouse Organs and Preparation of Protein Homogenates

All mouse studies were reviewed and approved by the Institutional Animal Care and Use Committee of the Children's Hospital of Philadelphia Research Institute. Wild-type C57BL/6J, Nos3$^{tm1Unc}$ (eNOS$^{-/-}$) C57BL/6J, and Lep$^{ob}$ (ob/ob) C57BL/6J adult mice were obtained from Jackson Laboratories. Food intake and bodyweight were recorded for ob/ob mice during the course of 4 weeks when the mice were being injected with PBS or 5 mM GSNO every 2 days. The average food intake was 42±9 and 41±10 g for PBS- and GSNO-injected ob/ob mice, respectively (n=4 mice per genotype). The average bodyweight change for the same period of time was 28.2±1.0 and 28.1±4.0 for ob/ob PBS- and ob/ob GSNO-injected mice, respectively (n=4 mice per genotype). Mice were anesthetized by $CO_2$, and blood was collected before being perfused through the left ventricle. Intact organs were collected, immediately frozen in liquid nitrogen, and stored at −80° C. until use.

Tissues were homogenized into 3 ml of lysis buffer [250 mM Hepes-NaOH (pH7.7) containing 1 mM diethylenetriamine pentaacetic acid, 0.1 mM neocuproine, 1% Triton X-100, and protease inhibitors] on ice with a Teflon pestle and a Jumbo Stirrer (Fisher Scientific). The homogenates were then centrifuged at 13,000 g for 30 minutes at 4° C. The soluble protein fraction was collected, and the protein concentration was determined by the Bradford assay. Sample preparation and generation of the negative control samples were performed as described (Doulias et al. (2010) Proc. Natl. Acad. Sci., 107:16958-16963).

Chemical Enrichment and Site-Specific Identification of the S-Nitrosocysteine Proteome A detailed experimental procedure for the preparation and activation of columns, homogenate preparation for reaction with organic mercury resin, has been described (Doulias et al. (2010) Proc. Natl. Acad. Sci., 107:16958-16963). Three biological replicates from each organ were analyzed. Each sample had a corresponding UV-pretreated negative control analyzed under identical conditions. The false identification rate was <6% for brain and <3% for all other organs. For washes, stringent conditions were selected due to the differences in lipid content among the six organs. Columns were initially washed with 50 bed volumes of 50 mM tris-HCl (pH 7.4) containing 300 mM NaCl and 0.5% SDS, followed by 50 bed volumes of the same buffer containing 0.05% SDS. Columns were washed with 50 bed volumes of 50 mM tris-HCl containing 300 mM NaCl (pH 7.4), 1% Triton X-100, and 1 M urea, followed by 50 bed volumes of the same buffer containing 0.1% Triton X-100 and 0.1 M urea. Finally, columns were washed with 200 bed volumes of water before proteins were eluted with 10 ml of 50 mM β-mercaptoethanol in water. Samples were concentrated and analyzed by gel-LC (liquid chromatography)-MS/MS analysis. For on-column digestion after the final wash with water, the columns were washed with 10 bed volumes of 0.1M ammonium bicarbonate. Bound proteins were subjected to digestion by the addition of Trypsin Gold (1 µg/ml) (Promega) in one bed volume of 0.1 M ammonium in the dark for 16 hours at room temperature. The resin was next washed with 40 bed volumes of 1M ammonium bicarbonate (pH 7.4) containing 300 mM NaCl, followed by 40 volumes of the same buffer without NaCl. Columns were then washed with 40 volumes of 0.1 M ammonium bicarbonate followed by 200 volumes of deionized water. To elute bound peptides, the resin was incubated with one bed volume of performic acid in water (performic acid is synthesized by reacting 1% formic acid and 0.5% hydrogen peroxide for at least 60 minutes at room temperature with rocking in a glass vial shielded from light) for 30 minutes at room temperature (Doulias et al. (2010) Proc. Natl. Acad. Sci., 107:16958-16963). Eluted peptides were recovered by washing the resin with one bed volume of deionized water. Eluates were stored at −80° C. overnight followed by lyophilization and resuspension into 300 µl of 0.1% formic acid. Peptide suspensions were transferred to low-retention tubes (Axygen), and the volume was reduced to 30 µl by speed vacuum. Twenty microliters of peptide suspension was transferred to a high-performance liquid chromatography vial and submitted for LC-MS/MS analysis.

The details for in-gel digestion and the conditions of MS/MS analysis have been provided previously (Doulias et al. (2010) Proc. Natl. Acad. Sci., 107:16958-16963; Keene et al. (2009) Proteomics 9:768-782). Post-MS analysis to generate the S-nitrosocysteine proteomes (Tables S1 to S6) has been performed as described with the following exception: Cysteine containing peptides that were not matched to proteins from the same organ were matched with proteins identified independently in other organs.

Subcellular localization was determined by either existing UniProt annotation (www.uniprot.org) or prediction by BaCelLo (gper.biocomp.unibo.it/bacello). Functional analysis to identify the biological functions that were most important was performed with UniProt and Fatigo (www.fatigo.org). The raw MS/MS data are deposited at www.research.chop.edu/tools/msms/spectra.pdf.

VLCAD Activity Assay

VLCAD enzymatic activity was assessed as described (Lehman et al. (1990) Anal. Biochem., 186:280-284). Briefly, ferricenium ion was used as an artificial electron acceptor for VLCAD-mediated palmitoyl-CoA dehydrogenation. Liver homogenate (final concentration of 0.03 μg/μl) or cell lysate (final concentration of 0.09 μg/μl) in 100 mM potassium phosphate buffer (pH 7.2) containing 0.2% Triton X-100 and 0.1 mM EDTA was mixed with 150 mM ferricenium ion, and the reaction was initiated by the addition of palmitoyl-CoA (the final volume of the assay was 130 μl). The decrease in ferricenium absorbance as a function of time at 300 nm was recorded, and the initial velocity ($V_o$) of the enzyme was determined from the slope of the curve from time 0 (when palmitoyl-CoA was added) to the time that corresponded to 5% of total change of absorbance. At least nine concentrations of palmitoyl-CoA, ranging from 0.015 to 2 mM, were used for the experimental determination of the apparent $V_{max}$ and $K_M$ of VLCAD for each animal. The experimental data were fitted to nonlinear regression to the Michaelis-Menten equation in GraphPad Prism software. A unit of enzyme activity is defined as the amount of enzyme that causes the reduction of 1 mmol of ferricenium per minute at room temperature ($\varepsilon$=4.3 mM$^{-1}$ cm$^{-1}$ at 300 nm) (Izai et al. (1992) J. Biol. Chem., 267:1027-1033). For the experiments to test the specificity of the assay, 10 mg of anti-VLCAD antibodies was preincubated with liver homogenate for 20 minutes. When UV photolysis was used to eliminate S-nitrosocysteines, the liver homogenate was illuminated under a conventional UV transilluminator for 10 minutes on ice. The measurement of specific activity of VLCAD in liver homogenates (FIG. 2H) and cell lysates (FIG. 4) was performed in the presence of 0.25 and 0.125 mM palmitoyl-CoA, respectively.

To quantify the fraction of S-nitrosylated VLCAD, the protein was captured onto the organomercury resin. After extensive washing, the bound proteins were eluted and probed with antibodies against VLCAD. After extensive washing, the bound proteins were eluted and probed with antibodies against VLCAD.

Liver Histology and Quantification of Triglyceride Concentrations

Formalin-fixed liver sections were stained with Trichrome Stain Kit (Sigma) according to the manufacturer's instructions. Triglycerides were extracted from liver according to the Folch method (Folch et al. (1957) J. Biol. Chem., 226:497-509). Serum and liver triglyceride concentrations were quantified with a triglyceride quantification kit following the manufacturer's instructions (Abcam).

Measurement of β-Oxidation of Fatty Acids

One milligram of protein suspension was added in 1 ml of Krebs-Ringer bicarbonate buffer containing fatty acid-free bovine serum albumin (2.5 mg/ml), 2.5 mM palmitic acid, 10 mM carnitine, and 4 mCi of 9,10-$^3$H-palmitoyl-CoA (Biomedicals). The mixture was rocked for 2 hours in the dark at 37° C., followed by Folch-based separation of 9,10-$^3$H-palmitoyl-CoA and $^3$H$_2$O (Folch et al. (1957) J. Biol. Chem., 226:497-509). The aqueous phase was collected, and proteins were precipitated by the addition of 10% TCA followed by centrifugation at 8000 g for 10 minutes at room temperature. Remaining radioactive palmitoyl-CoA was eliminated by strong anion exchange chromatography with AG 1-X8 formate resin (Life Science). The effluent containing the $^3$H$_2$O was collected and used for scintillation counting. Each experiment was coupled with a background measurement, a sample containing no protein. The background count number was subtracted from each measurement corresponding to analysis samples.

Site-Directed Mutagenesis to Generate the C238A VLCAD Mutant

The QuikChange® Lightning Site-Directed Mutagenesis Kit (Agilent Technologies) was used to introduce single amino acid mutations in complementary DNA encoding VLCAD. A cysteine-to-alanine mutant at amino acid position 238 was generated with Ex-Mm01013-M14 (hereinafter referred to as pVLCAD-3×FLAG®), a plasmid encoding mouse VLCAD fused to three FLAG® tags in the C-terminal region of the protein (GeneCopoeia), as a template. The forward primer 5'-TCAGCCATACCCAGCCCCGCTG-GAAAATATTACACTCTC-3' (SEQ ID NO: 1) and the reverse primer 5'-GAGAGTGTAATATTTTCCA-GCGGGGCTGGG TATGGCTGA-3' (SEQ ID NO: 2) were used to substitute an alanine codon for a cysteine codon in pVLCAD-3×FLAG®, thereby generating pVLCAD-C238A-3×FLAG®. The sequence of both pVLCAD-3× FLAG® and pVLCAD-C238A-3×FLAG® was verified before use in subsequent experiments.

Cell Culture, Transfection, and Treatment with GSNO

Hepa 1 to 6 cells were grown in Dulbecco's modified Eagle's medium (DMEM) containing 10% fetal bovine serum, 2 mM glutamine, penicillin (100 U/ml), and streptomycin (100 ng/ml) at 37° C. in air with 5% CO$_2$. Cells were plated at a density of 5×10$^4$ cells/cm$^2$ and cultured under normal conditions for 24 hours. Cells were transfected with FLAG®-tagged wild-type VLCAD or FLAG®-tagged C238A VLCAD with Lipofectamine® 2000 reagent (Life Technologies) according to the protocol provided by the manufacturer. Forty-eight hours after transfection, the growth medium was replaced with serum-free DMEM, and 250 mM freshly prepared GSNO was added for 30 minutes, after which the cells were extensively washed with PBS. Cell lysates were obtained immediately or 60, 120, and 240 minutes after the removal of GSNO. The samples were protected from UV light exposure. Lysates were assayed for protein concentration, and equal amounts of protein per sample were used for organic mercury-assisted capture.

Structure Generation of S-Nitrosylated Cysteine and Normal Mode Analysis

The crystal structure of human VLCAD was downloaded from PDB (ID 2UXW). Disordered or missing residues were completed with the Mutagenesis tool in PyMol (www.pymol.org). S-nitrosocysteine was generated with the "S-nitrosator" Python script from the Timerghazin laboratory in the Molecular Modeling Toolkit. S-nitrosator uses the coordinates of thioredoxin and χ3 values calculated from PCM-ONIOM (PBEO/def2-TZVPPD:AmberFF) calculation of an S-nitrosocysteine residue in an α helix content. ElNémo (Suhre et al. (2004) Nucleic Acids Res., 32:W610-W614) was used to observe the 100 lowest frequency modes, and perturbed models were generated for the first five nontrivial modes of VLCAD. Residue mean square displacement (r$^2$) was used to identify protein movement.

Statistical Analysis

Data were analyzed with GraphPad Prism 5.0d software. All normally distributed data were displayed as means±SD. Groups were analyzed by one-way ANOVA.

Results

A Mouse S-Nitrosocysteine Proteome

In wild-type mouse brain, heart, kidney, liver, lung, and thymus, 1011 S-nitrosocysteine-containing peptides were identified on 647 proteins. Extensive literature searches indicated that this expanded S-nitrosocysteine proteome identified 46 proteins previously reported to be modified under physiological conditions and uncovered 971 previously unknown sites of endogenous S-nitrosylation. In all six organs, the number of S-nitrosylation sites exceeded the number of proteins, indicating a potential role of poly-S-nitrosylation in the regulation of protein function in vivo (Simon et al. (1996) Proc. Natl. Acad. Sci., 93:4736-4741). Comparison of the proteins identified in the six organs in at least three biological replicates for each organ revealed that, on average, 72% of the proteins were identified in more than one organ, indicating that similar patterns of S-nitrosylation serve global functions in vivo. Moreover, these data indicated that the methodologies used to acquire these proteomes were accurate and reproducible. Proteins identified only in one organ ranged from 21 to 46%, indicating that S-nitrosylation can also serve organ-specific roles. The dependency of the sites of S-nitrosylation in vivo to nitric oxide generated by eNOS was explored by analyzing the endogenous sites of modification in eNOS null mice (eNOS$^{-/-}$) in the same organs. eNOS substantially contributed to the endogenous S-nitrosocysteine proteome because S-nitrosylation of 47 to 87% of the proteins identified required the presence of eNOS. The brain and the heart had the lowest dependency on eNOS activity compared to the other organs, indicating the contribution of other isoforms such as neuronal nitric oxide synthase for S-nitrosylation of proteins in these organs. The absence of a substantial number of S-nitrosocysteine peptides in organs from eNOS$^{-/-}$ mice reinforced the accuracy of the methodologies in identifying this S-nitrosocysteine proteome.

An overview of the subcellular localization of the S-nitrosoproteome revealed a tissue-wide significant enrichment for cytosolic and mitochondrial proteins as compared to the entire mouse proteome. S-nitrosylation sites in proteins in cellular membranes and nucleus were underrepresented. The underrepresentation of membrane proteins may reflect methodological issues because the tissue homogenization method was not optimized for extraction of membrane proteins. S-nitrosylation of proteins also occurs in the nucleus, and the discovery of additional sites in nuclear proteins reinforces the potential importance of S-nitrosylation in signaling and transcriptional regulation (Kornberg et al. (2010) Nat. Cell Biol., 12:1094-1100). Twenty percent to 25% of the S-nitrosoproteome in the brain, kidney, liver, lung, and thymus consisted of mitochondrial proteins, whereas 56% of the modified proteins were localized to mitochondria in the mouse heart. The mitochondrial proteomes were more than 70% dependent on eNOS activity with the exception of the heart, where only 36% of the proteome requires eNOS-derived nitric oxide for S-nitrosylation. The lower dependency of S-nitrosylation on eNOS activity in heart mitochondria indicates the presence of another functional NOS isoform. Functional classification of the S-nitrosoproteome revealed key metabolic pathways in which S-nitrosylated enzymes play a central role. It was found that a substantial number of enzymes that regulate glycolysis, gluconeogenesis, pyruvate metabolism, tricarboxylic acid (TCA) cycle, oxidative phosphorylation, amino acid metabolism, ketone body formation, and fatty acid metabolic pathways were S-nitrosylated, most of which were not identified as S-nitrosylated in eNOS$^{-/-}$ mice. This finding is consistent with reports indicating that the eNOS null mice have impaired metabolic activity (Schild et al. (2008) Biochim. Biophys. Acta, 1782:180-187; Mohan et al. (2008) Lab. Invest., 88:515-528). Therefore, it appears that protein S-nitrosylation provides the mechanistic link that couples eNOS activity and regulation of metabolism.

Regulation of the Enzymatic Activity of Very Long Chain Acyl-CoA Dehydrogenase by S-Nitrosylation Clustering of proteins that participate in fatty acid metabolism was apparent in this analysis. In the mouse liver, S-nitrosylated proteins are clustered in a network that encompasses liver responses to the hormone leptin (Doulias et al. (2010) Proc. Natl. Acad. Sci., 107:16958-16963). Here, it was found that very long chain acyl-coenzyme A (CoA) dehydrogenase (VLCAD), which catalyzes the rate-limiting step in the β-oxidation of fatty acids, was S-nitrosylated in wild-type mouse liver but not in the livers of mice lacking leptin (ob/ob) or eNOS$^{-/-}$ mice (FIG. 1). The biological effect of S-nitrosylation on VLCAD activity and fatty acid metabolism in the liver, which is a major metabolic organ, was investigated.

Figure 2A:
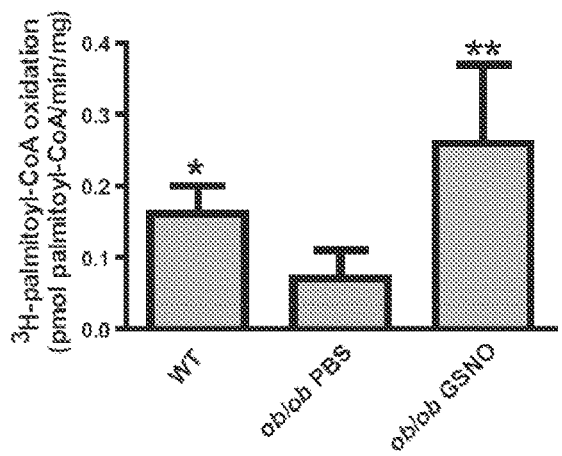
FIG. 2A provides a graph of the rate of $^3$H-labeled palmitoyl-CoA oxidation in liver homogenates from wild-type and ob/ob mice. *P<0.05 by analysis of variance (ANOVA) with Bonferroni post hoc test between wild-type and ob/ob PBS-treated mice (n=4 mice). **P<0.01 by ANOVA with Bonferroni post hoc test between ob/ob PBS- and ob/ob GSNO-treated mice (n=4 mice).
Figure 2B:
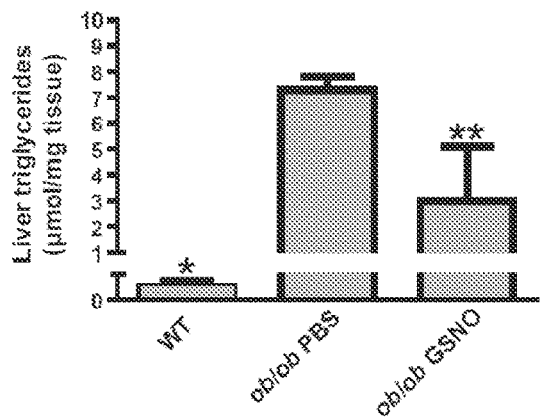
FIG. 2B shows liver triglyceride measurements in wild-type mice, PBS-treated ob/ob mice, and GSNO-treated ob/ob mice. *P<0.0001 by ANOVA with Bonferroni post hoc test between wild-type and ob/ob PBS-treated mice (n=4 mice). **P<0.005 by ANOVA with Bonferroni post hoc test between ob/ob PBS- and ob/ob GSNO-treated mice (n=4 mice).
Figure 2C:
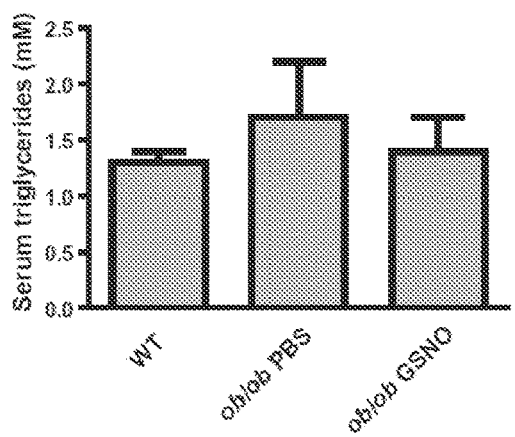
FIG. 2C shows serum triglyceride measurements in wild-type mice, PBS-treated ob/ob mice, and GSNO-treated ob/ob mice. No statistical difference (n=4 mice).

Leptin-deficient mice develop liver steatosis spontaneously under normal chow diet starting at 4 to 5 weeks of life that is characterized by a diminished rate of palmitate oxidation and accumulation of fat droplets in the form of triglycerides within the hepatocytes (Brix et al. (2002) Mol. Genet. Metab., 75:219-226; de Oliveira et al. (2008) J. Am. Coll. Nutr., 27:299-305). The rate of $^3$H-labeled palmitoyl-CoA oxidation by liver homogenates in ob/ob mice was 47% of the rate in wild-type mice (FIG. 2A). This significant reduction in the rate of palmitoyl-CoA oxidation indicated a deficiency in mitochondrial β-oxidation of fatty acids. Based on observations that showed reversal of hepatic steatosis in ob/ob mice by delivery of S-nitroso-N-acetyl cysteine (de Oliveira et al. (2008) J. Am. Coll. Nutr., 27:299-305), 5-week-old ob/ob mice were injected intraperitoneally with S-nitrosoglutathione (GSNO). GSNO was used to deliver nitric oxide equivalents because of the extensive use of this pharmacological agent in cellular models to modify proteins by S-nitrosylation despite limited cellular permeability (Hara et al. (2005) Nat. Cell Biol., 7:665-674; Chung et al. (2004) Science 304:1328-1331). GSNO-injected ob/ob mice exhibited a similar palmitoyl-CoA oxidation rate as wild-type mice and a significantly increased rate over phosphate-buffered saline (PBS)-injected ob/ob mice (FIG. 2A). Moreover, the restoration of palmitoyl-CoA oxidation in GSNO-injected ob/ob mice was associated with a significant reduction of the concentration of liver triglycerides. The liver triglyceride concentration in ob/ob mice injected with PBS was significantly higher than in wild-type mice, and treatment of ob/ob mice with GSNO significantly lowered the liver triglyceride concentration (FIG. 2B). The serum triglyceride concentrations were similar in wild-type mice, PBS-treated ob/ob mice, and GSNO-treated ob/ob mice (FIG. 2C). The restoration of palmitoyl-CoA oxidation in GSNO-injected ob/ob mice was also corroborated by histological evaluation of liver slices, which showed fewer fat deposits in GSNO-injected than in PBS-injected ob/ob mice (FIG. 2G).

Figure 1B:
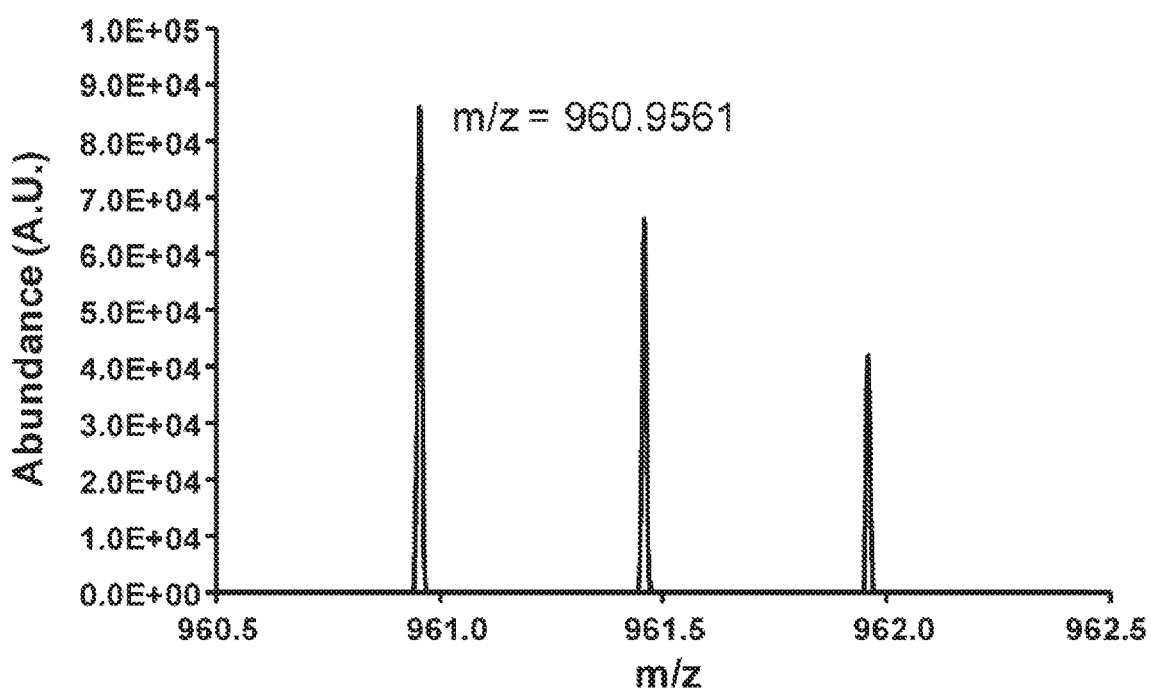
Figure 1C:
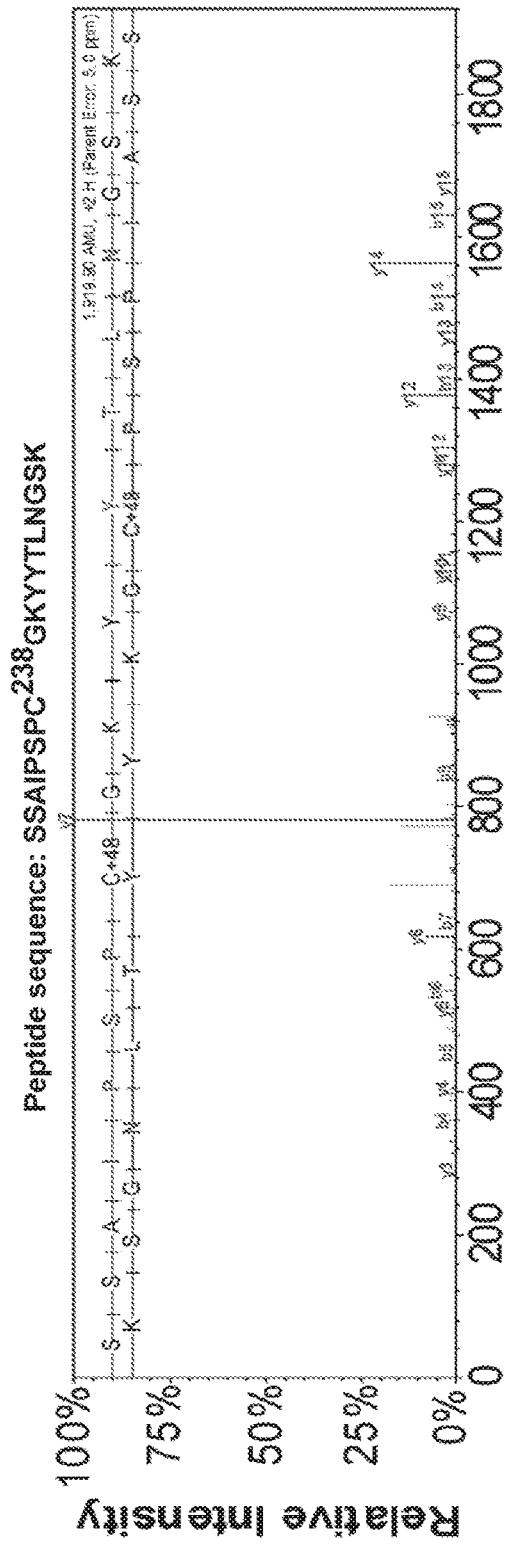
Figure 1D:
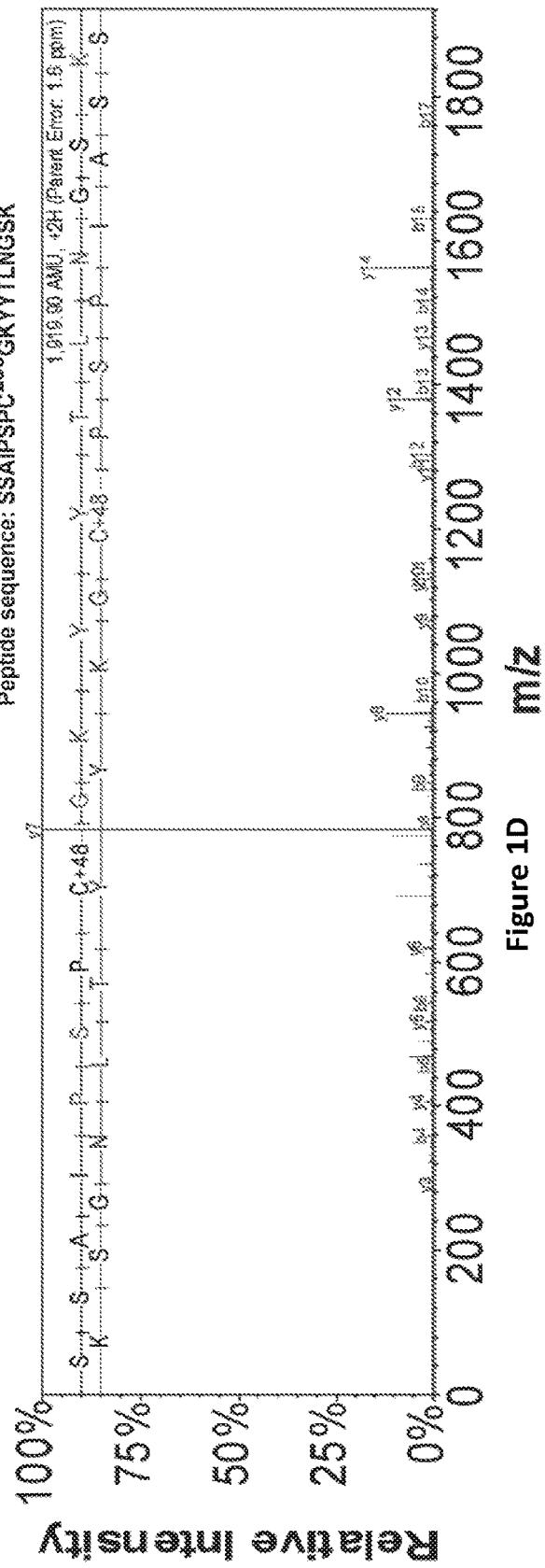

MS/MS analysis localized the site of VLCAD modification to Cys238 in both wild-type and GSNO-injected ob/ob mice (FIGS. 1A and 1B). It was also confirmed that VLCAD was not modified by S-nitrosylation in eNOS$^{-/-}$ mice but was readily modified ex vivo at cysteine residue Cys238 by treating liver homogenates with GSNO (FIGS. 2H and 2I).

Figure 2D:
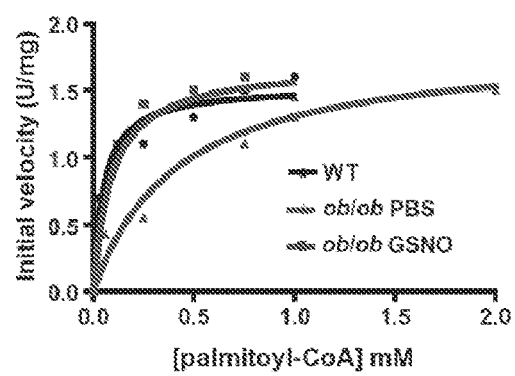
FIG. 2D provides representative measurements of VLCAD initial velocity measured as a function of palmitoyl-CoA concentration in liver homogenates from wild-type, ob/ob PBS, and ob/ob GSNO mice.
Figure 2E:
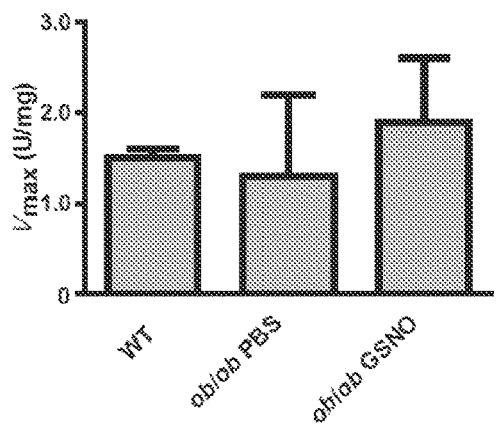
FIGS. 2E and 2F provides kinetic analysis of VLCAD enzymatic activity reveals similar $V_{max}$ but significantly higher KM in PBS-treated ob/ob mouse liver as compared to wild-type and GSNO-treated ob/ob mouse liver. *P<0.05 by ANOVA with Bonferroni post hoc test (n=3 biological replicates).
Figure 2F:
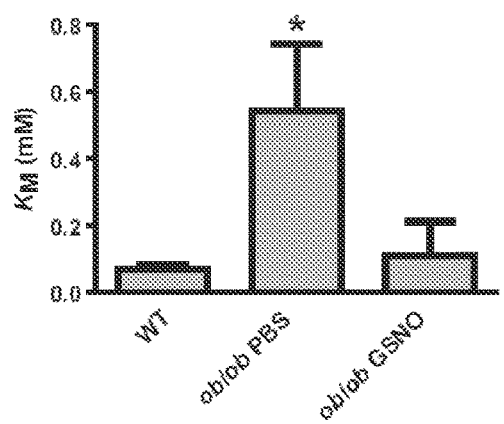
Figure 2G:
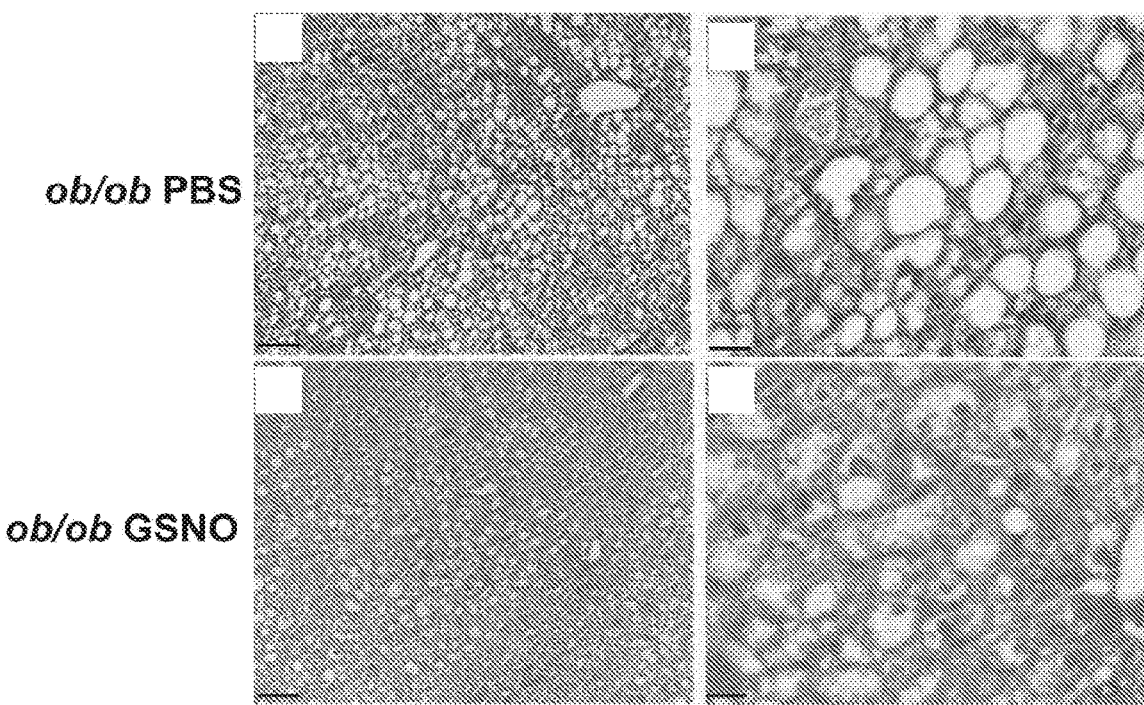
FIG. 2G provides images of trichrome staining of liver tissue showing diminished fatty acid deposition in ob/ob mice treated with GSNO (bottom)
Figure 2H:
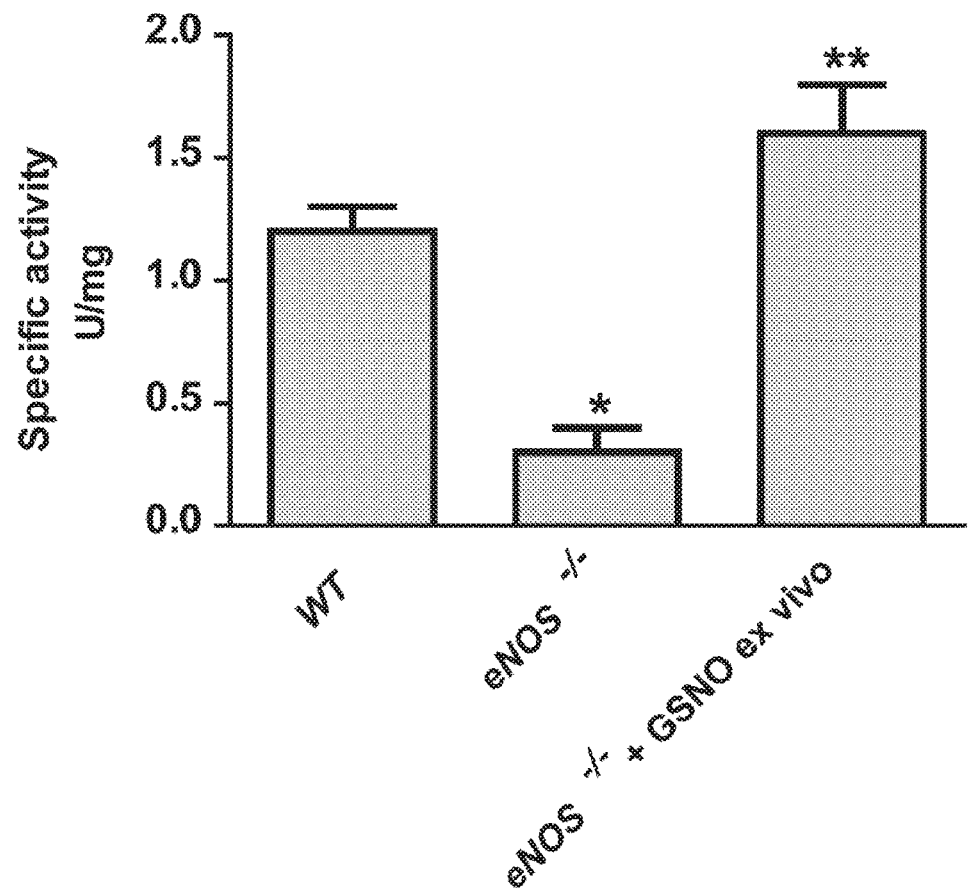
FIG. 2H shows VLCAD specific activity determined by monitoring palmitoyl-CoA (0.25 mM) mediated reduction of ferrocenium ion in liver homogenates from wild type and eNOS$^{-/-}$ mouse. The specific activity of eNOS$^{-/-}$ was significantly lower than wild-type or eNOS$^{-/-}$ liver tissue treated with 5 μM GSNO 30 minutes prior to the assay. *p<0.0001, **p<0.05 by ANOVA with Bonfferoni's post hoc test. N=3 biological replicates.
Figure 3A:
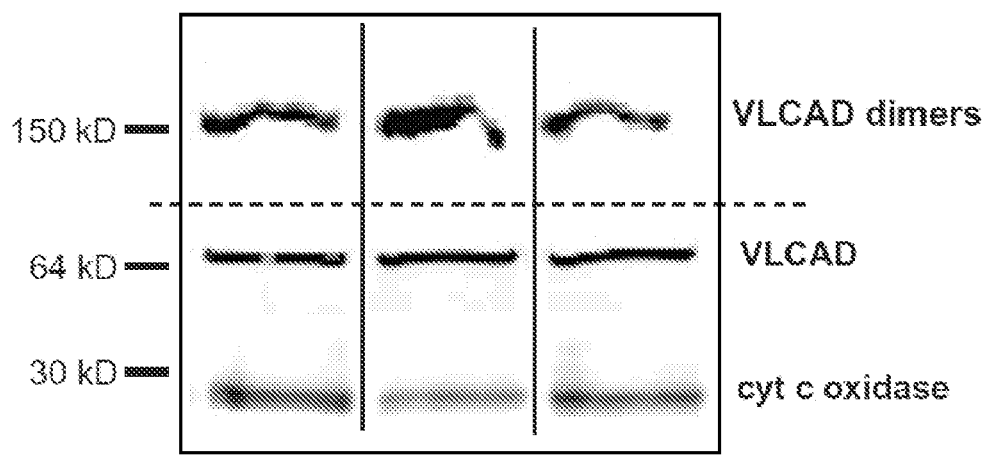
FIG. 3A provides representative Western blots assessing VLCAD in native gel (top panel) and in SDS gel (middle panel). Noncontiguous lanes from a single experiment are indicated by black lines.
Figure 3B:
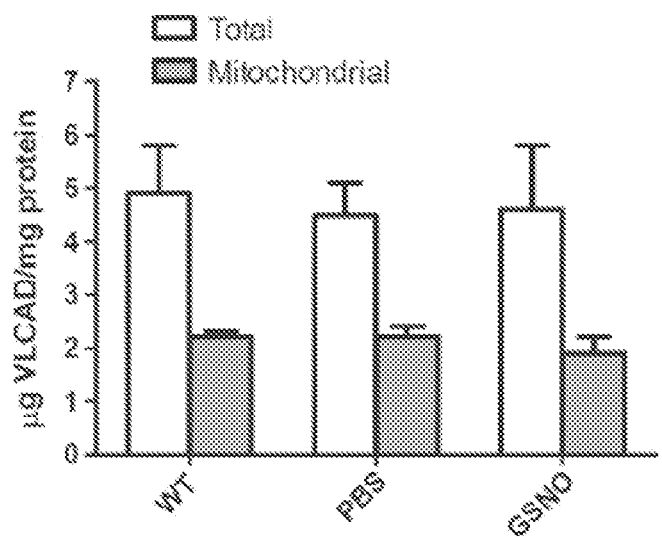
FIG. 3B shows the quantification of abundance of VLCAD in SDS gels under reducing conditions in total liver homogenates and enriched mitochondria fractions from liver. No statistical difference by ANOVA. n=3 different mice. cyt c, cytochrome c.

The S-nitrosylation of VLCAD was associated with an increase in acyl dehydrogenase-mediated oxidation of palmitoyl-CoA in GSNO-treated ob/ob mouse liver (FIGS. 2D, 2J, and 2K). This increase was sensitive to UV photolysis and was abolished by the inclusion of specific antibodies against VLCAD (FIG. 2J). Analysis of Michaelis-Menten kinetics (FIG. 2D) revealed that the $V_{max}$ of VLCAD was similar in wild-type, PBS-injected, and GSNO-injected ob/ob mice (FIG. 2E). However, the apparent Michaelis constant ($K_M$) value measured in homogenates from PBS-injected ob/ob mice was more than fivefold higher than in those from wild-type mice and GSNO-injected ob/ob mice (FIG. 2F). The $K_M$ for VLCAD enzymatic activity also increased five-fold in eNOS$^{-/-}$ liver homogenates treated ex vivo with GSNO compared to untreated eNOS$^{-/-}$ liver homogenate (FIG. 2H). Quantification of the abundance of VLCAD protein in liver homogenates and enriched mitochondria preparations indicated no differences in abundance among wild-type, PBS-injected, and GSNO-injected ob/ob mice (FIGS. 3A and 3B). Furthermore, native gel electrophoresis revealed equal abundance of VLCAD dimers in the mitochondria fractions from all three groups of mice (FIG. 3A, upper panel). Therefore, these data indicate that S-nitrosylation decreases the KM of VLCAD.

Figure 3C:
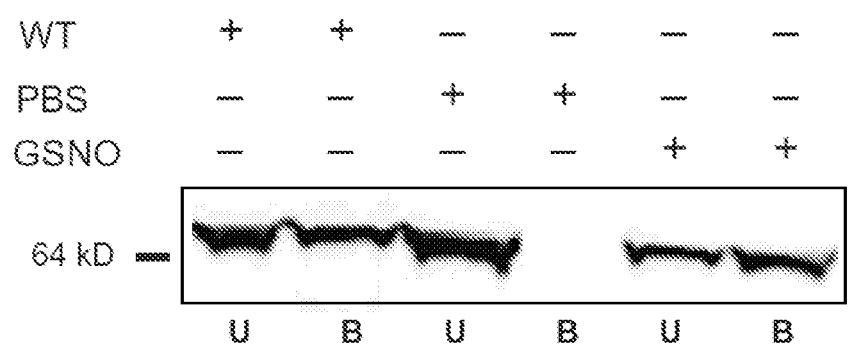
FIG. 3C provides a representative Western blot for VLCAD in liver homogenates eluted from organomercury resin. The signal intensity was used to determine the abundance of S-nitrosylated VLCAD in the bound (B) fraction and the unmodified VLCAD present in the unbound (U) fraction. The data were repeated in two independent liver homogenates.

Quantification of the fraction of S-nitrosylated VLCAD indicated that in GSNO-treated mice, 25±3% of VLCAD molecules in liver were S-nitrosylated. These findings confirm the MS/MS analysis showing S-nitrosylation of VLCAD in wild-type and GSNO-treated mouse liver but not in PBS-treated ob/ob mouse liver (FIG. 3C). Because the concentrations of VLCAD protein were similar in PBS- and GSNO-treated ob/ob mice and on average the steady-state abundance of S-nitrosylated VLCAD was 25% of the total protein, S-nitrosylation can increase the catalytic efficiency ($k_{cat}/K_M$) (Koshland, D. E. (2002) Bioorg. Chem., 30:211-213) of VLCAD 29-fold as compared to the unmodified protein. This substantial increase in catalytic efficiency can provide efficient removal of fatty acids in ob/ob mouse liver.

Figure 4A:
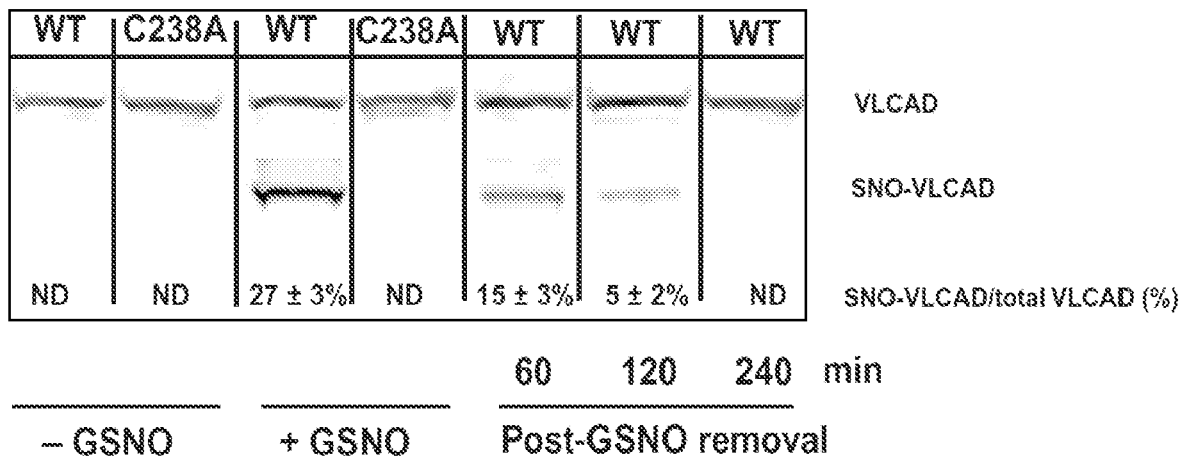
FIG. 4A provides representative Western blot analysis of unbound (VLCAD) and bound fractions (SNO-VLCAD) collected after mercury-assisted capture in cell lysates. Hepa 1 to 6 cells transiently expressing either FLAG®-tagged wild-type or C238A VLCAD were exposed to GSNO. The unbound fraction indicates the abundance of the unmodified protein. The bound fraction indicates the abundance of S-nitrosylated VLCAD. The abundance of both was determined by using a calibrated antibody binding curve using purified VLCAD. The fraction of S-nitrosylated VLCAD as percentage of VLCAD is indicated. ND, not detected. n=3 biological replicates. Noncontiguous lanes from a single experiment are indicated by black lines.
Figure 4B:
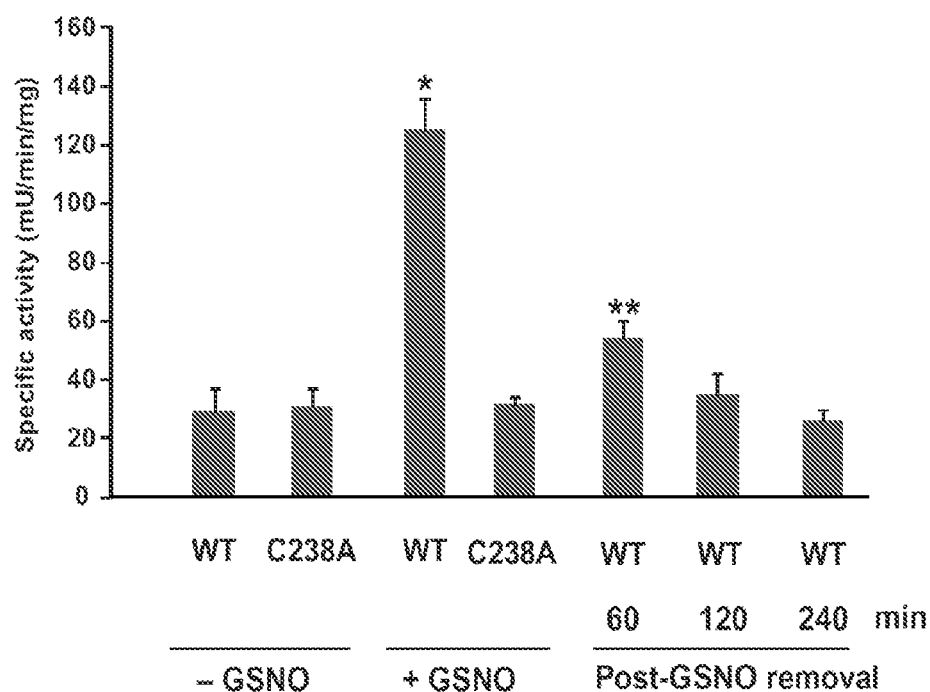
FIG. 4B shows the specific activity of VLCAD was significantly higher in GSNO-treated cells expressing wild-type VLCAD but not in GSNO-treated cells expressing equivalent amount of C238A VLCAD mutant protein. *P<0.001, **P<0.05 by ANOVA with Bonferroni post hoc test. n=3 biological replicates.

Additional evidence for the functional consequences of S-nitrosylation of VLCAD was obtained in mouse hepatocytes transiently expressing wild-type VLCAD or a point mutant that could not be S-nitrosylated (C238A). GSNO treatment resulted in S-nitrosylation of 27±3% of wild-type VLCAD (FIG. 4A) concomitant with a fivefold increase of VLCAD-specific activity (FIG. 4B). Under the same experimental conditions, the C238A VLCAD mutant was not S-nitrosylated, and its basal activity did not change in response to GSNO treatment (FIGS. 4A and 4B). Upon removal of GSNO from the media and extensive washing, both the abundance of S-nitrosylated VLCAD and the enzymatic-specific activity declined over time (FIGS. 4A and 4B). These data indicate that S-nitrosylation of VLCAD at Cys$^{238}$ is necessary for the regulation of its enzymatic activity, and this process is reversible, possibly controlled through denitrosylation.

Figure 5A:
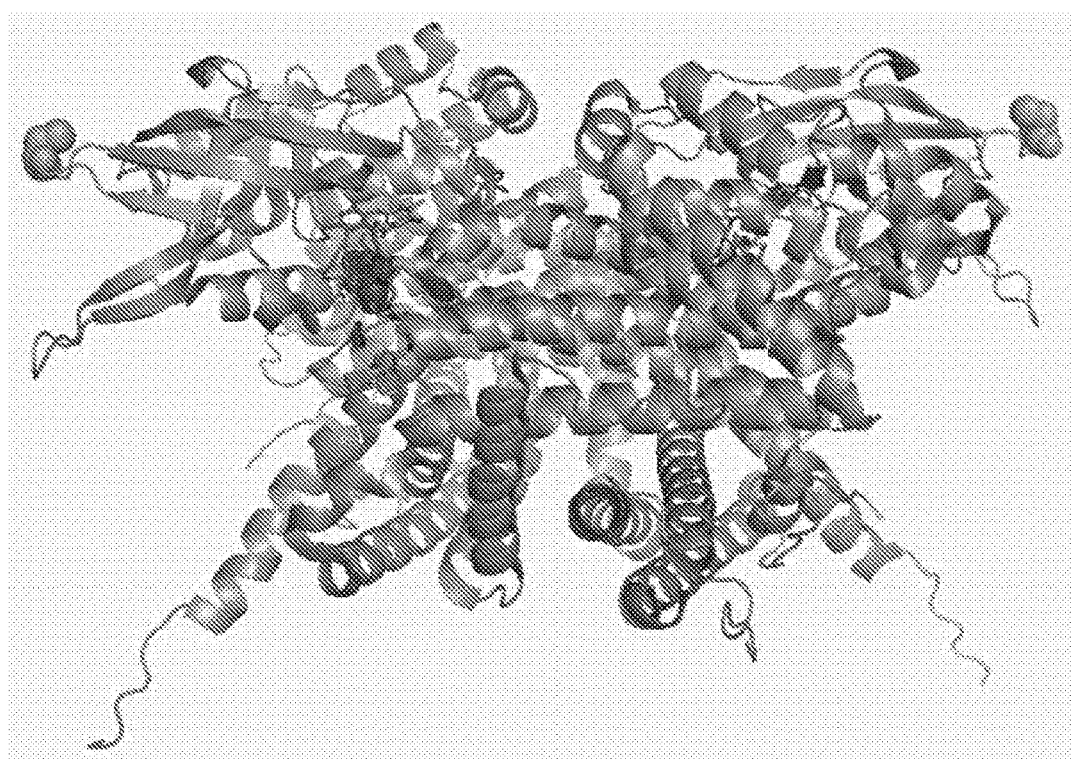
FIG. 5A provides the crystal structure of VLCAD dimer with the site of S-nitrosylation on Cys$^{238}$ annotated in gold on both monomers. Note that Cys$^{238}$ is in a loop, a secondary conformation that typically shows increased flexibility.
Figure 5B:
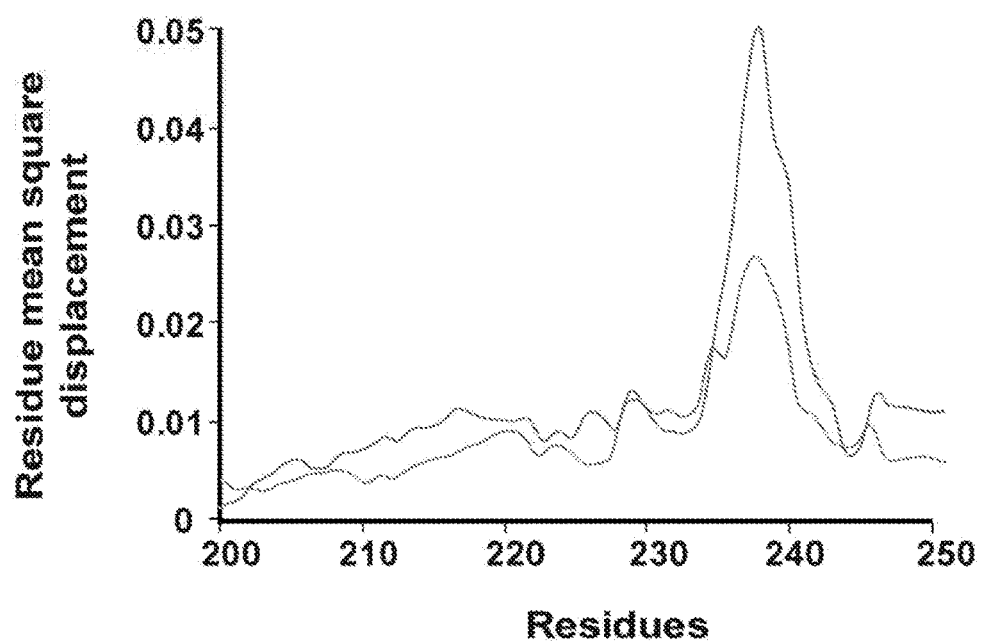
FIG. 5B shows higher frequency mode indicates extensive movement of Cys$^{238}$ upon S-nitrosylation. Normal mode analysis of unmodified and SNO-VLCAD using the web interface ElNémo (igs-server.cnrs-mrs.fr/elnemo/index.html). The bottom line depicts the $R^2$ values for the amino acid residues of the unmodified VLCAD whereas the top line depicts the values for the same residues of the S-nitrosylated VLCAD. Note the higher $R^2$ value for the S-nitrosocysteine 238 compared to the unmodified cysteine indicative of the enhanced movement of Cys$^{238}$ upon S-nitrosylation.

Molecular dynamic simulation was used to gain insight into the effect of S-nitrosylation on VLCAD structure. Quantum mechanics/molecular mechanics calculations was used initially to generate the S-nitrosocysteine residue at position 238 within the protein structure of VLCAD [ProteinDataBank (PDB) ID2UXW] (FIG. 5A). Examination of the lowest frequency normal modes, which indicate large global or collective motions of a protein, did not indicate that S-nitrosylation induced large conformational changes. Examination of higher frequency modes to investigate smaller local motions that might occur near the binding site revealed a difference in the movement of atoms in response to S-nitrosylation of Cys238 (FIG. 5B). Cys238 resides in a loop, and loops generally represent flexible regions of a protein. Therefore, the data indicate that S-nitrosylation enhances loop flexibility, resulting in increased protein movement, which in turn facilitates substrate binding and therefore lowers the $K_M$ of VLCAD. Cys$^{238}$ was ≥30 Å from the substrate binding site, indicating that longer-range motions can influence the ability of the enzyme to bind substrate.

Cysteine S-nitrosylation is a nitric oxide-derived posttranslational modification that modulates protein activity, protein-protein interactions, and subcellular localization under physiological and pathological conditions (Stamler et al. (2001) Cell 106:675-683; Hess et al. (2005) Nat. Rev. Mol. Cell Biol., 6:150-166; Benhar et al. (2008) Science 320:1050-1054; Jaffrey et al. (2001) Nat. Cell Biol., 3:193-197; Kornberg et al. (2010) Nat. Cell Biol., 12:1094-1100; Matsushita et al. (2003) Cell 115:139-150; Mitchell et al. (2005) Nat. Chem. Biol., 1:154-158; Cho et al. (2009) Science 324:102-105; Mannick et al. (2001) J. Cell Biol., 154:1111-1116). Applying site-specific mapping of S-nitrosocysteine residues in wild-type mouse tissue, widespread modification of proteins participating in metabolic pathways and a significant localization of modified proteins in the mitochondria was identified. This selective localization is consistent with several reports indicating functional roles for nitric oxide in mitochondrial biology (Brown et al. (1994) FEBS Lett., 356:295-298; Kobzik et al. (1995) Biochem. Biophys. Res. Commun., 211:375-381; Nisoli et al. (2005) Science 310:314-317) and specifically for the heart, where protein S-nitrosylation protects the heart from ischemia-reperfusion injury (Prime et al. (2009) Proc. Natl. Acad. Sci., 106:10764-10769; Lima et al. (2009) Proc. Natl. Acad. Sci., 106:6297-6302; Kohr et al. (2012) Circ. Res., 111:1308-1312). Delivery of nitric oxide donors specifically to the heart increases the overall abundance of mitochondrial S-nitrosylated proteins and protects from ischemic injury (Prime et al. (2009) Proc. Natl. Acad. Sci., 106:10764-10769; Lima et al. (2009) Proc. Natl. Acad. Sci., 106:6297-6302; Kohr et al. (2012) Circ. Res., 111:1308-1312). Despite these important biological contributions of nitric oxide in the functional regulation of mitochondria and metabolism, the identification of S-nitrosylated mitochondrial proteins is limited. The identification of specific sites of S-nitrosylation in mitochondrial proteins across six different mouse tissues provides a substantial advance that facilitates mechanistic studies to uncover molecular and biochemical pathways for nitric oxide-mediated regulation of bioenergetics and metabolism. Similar to other posttranslational modifications, S-nitrosylation is a dynamic process, and several pathways that reverse this posttranslational modification have been described (Benhar et al. (2008) Science 320:1050-1054). Therefore, the current S-nitrosocysteine proteome may represent a portion of the endogenously modified proteins under normal physiological conditions.

To explore the biological role of S-nitrosylation in vivo, fatty acid metabolism in the liver, a major metabolic organ in the body, was studied. Diet, adipose tissue, and de novo lipogenesis are the major sources of fatty acids for the liver. Potential fates of fatty acids in the liver include esterification to triglycerides, which can be stored or packaged with apolipoprotein B-100 for export as part of very low density lipoprotein particles. Fatty acids can be also converted to phospholipids or transformed to acyl-carnitines for transport into mitochondria, where they undergo β-oxidation (Cohen et al. (2011) Science 332:1519-1523). Any process that increases the input or decreases the output or metabolism of fatty acids potentially contributes to the development of liver steatosis (Cohen et al. (2011) Science 332:1519-1523). β-Oxidation is a four-step enzymatic cycle, and each turn of the cycle shortens the length of the fatty acid by two carbon atoms, which is critical for efficient use of fatty acids. VLCAD catalyzes the first step in β-oxidation, accounting for about 80% of palmitate dehydrogenase activity in human liver and nearly 70% of palmitate oxidation in mouse liver (Aoyama et al. (1995) J. Clin. Invest., 95:2465-2473; Djordjevic et al. (1994) Biochemistry 33:4258-4264; Strauss et al. (1995) Proc. Natl. Acad. Sci., 92:10496-10500). VLCAD is a homodimer consisting of 67-kD subunits and is embedded in the inner mitochondria membrane (Aoyama et al. (1995) J. Clin. Invest., 95:2465-2473; Djordjevic et al. (1994) Biochemistry 33:4258-4264; Strauss et al. (1995) Proc. Natl. Acad. Sci., 92:10496-10500). The enzymatic activity of VLCAD appears to be regulated by protein abundance and phosphorylation of $Ser^{586}$ (Kabuyama et al. (2010) Am. J. Physiol. Cell Physiol., 298:C107-C113). The data presented hereinabove indicate that S-nitrosylation of VLCAD at $Cys^{238}$ through eNOS-derived nitric oxide results in reversible activation of enzymatic activity through conformational changes that alter the $K_M$ of the enzyme and can substantially influence the in vivo β-oxidation of fatty acids. Overall, the global analysis of S-nitrosylated proteins in mouse tissues revealed that this posttranslational modification can profoundly influence cellular metabolic processes and mitochondria function.

Example 2

Nitric oxide (NO) regulates mitochondrial metabolism under normal and pathological conditions. One of the mechanisms by which nitric oxide achieve its regulatory effect is through the S-nitrosylation of cysteine residues in proteins. As shown hereinabove, 25% of VLCAD molecules are S-nitrosylated at cysteine 238 in vivo (mouse models). S-nitrosylation lowers the apparent Km of VLCAD by 5-fold and improves the catalytic efficiency by 29-fold as compared to the unmodified enzyme. In an animal model that resembles features of the human disease (low VLCAD activity, low β-oxidation rate, hepatic accumulation of triglycerides), S-nitrosylation of VLCAD restored enzymatic activity, normalized β-oxidation rate and diminished the steatotic phenotype. Based on these results, S-nitrosylation of missense mutated human VLCAD will improve its catalytic efficiency and will positively affect the outcome of the disease.

Figure 6A:
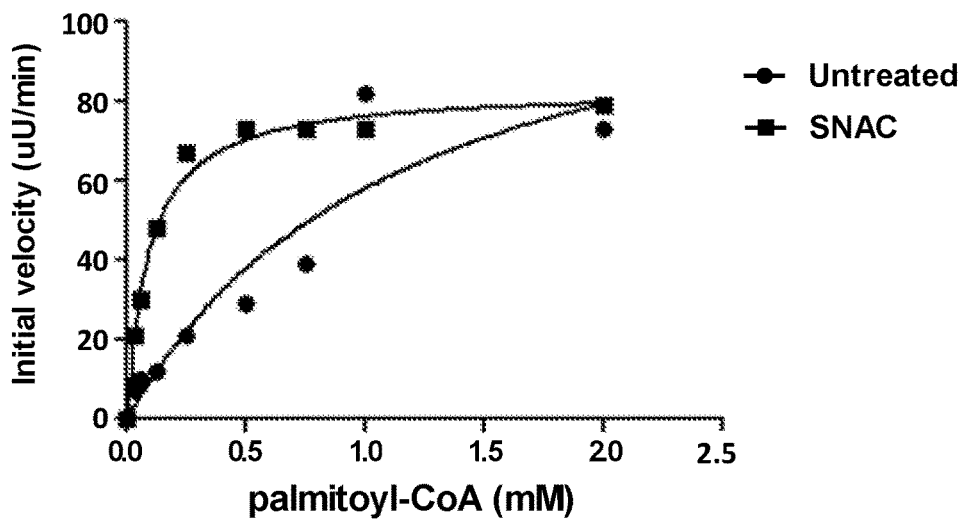
FIGS. 6A and 6B provide graphs of the VLCAD kinetic parameters of cell lines 1 and 2, respectively. Five μg of cell lysate were mixed with 150 μM ferrocenium followed by the addition of the indicated concentrations of palmitoyl-CoA. The decrease in ferricenium absorbance as a function of time at 300 nm was recorded and the initial velocity of the enzyme was determined from the slope of the curve from time 0 to the time that corresponded to 5% of total change of absorbance.
Figure 6B:
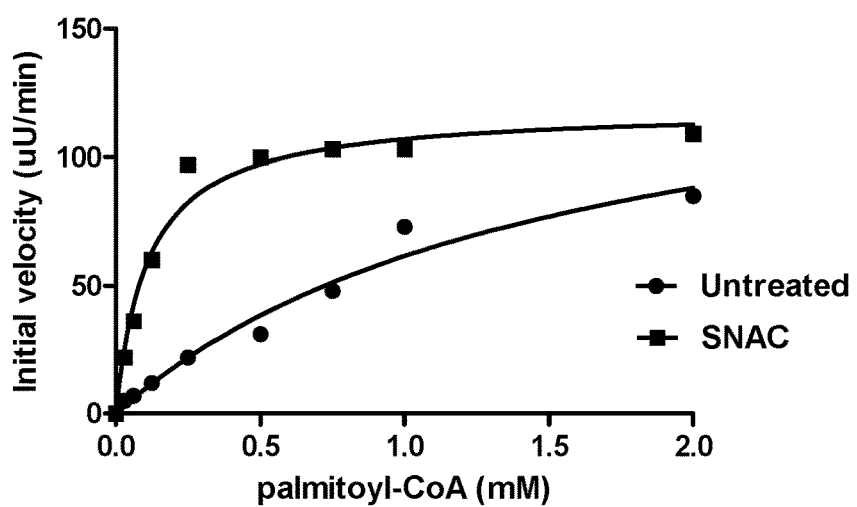

To test this conclusion, four human fibroblast lines carrying pathologic VLCAD mutations were used (Table 1). Cells were exposed to 100 µM N-acetylcysteine or S-nitroso-N-acetyl-cysteine (SNO-NAC) for 30 minutes and the S-nitrosylation status of VLCAD was determined by organomercury-assisted capture and mass spectrometry as described hereinabove. Using lysates from cell lines 1 and 2, it was determined that VLCAD was modified on cysteine 237 (human VLCAD has one fewer amino acid) after SNO-NAC treatment. VLCAD enzymatic activity was assessed in cell lysates by monitoring the ferrocenium reduction in the presence of palmitoyl-CoA as substrate for the enzyme. FIG. 6 presents the Michaelis-Menten traces for cell lines 1 and 2 showing that S-nitrosylation of VLCAD has a prominent effect on the Km (14 fold lower as compared to the unmodified enzyme) and at a lesser extent on $V_{max}$.

TABLE 1

Missense mutations on VLCAD. Each cell line had two mutations.

| Patient 1 | G185S | G295E |
| Patient 2 | P91Q | G193R |
| Patient 3 | P89S | A536fsX550 |
| Patient 4 | N122D | N112D |

A detailed kinetics analysis was performed for the other mutants as well as for the wild type VLCAD (Table 2). Low mitochondrial fatty acid oxidation (mFAO) capacity and VLCAD activity was documented in VLCAD-deficient fibroblasts treated with NAC as compared to control cells. For Table 2, initial velocity (Vo) was determined in the linear part of reaction curve by calculating the slope from time 0 to the time corresponding to 5% loss of initial absorbance. For determination of Km and Vmax, 10 concentrations of palmitoyl-CoA ranging from 0.015 to 2 mM were used. mFAO rate was determined by quantifying $^3H_2O$ released in the culture medium of cells incubated with $^3H$-palmitate. The table presents the average values of two different experiments. The two values do not differ by more than 10%.

In all cases the protein follows typical Michaelis-Menten kinetics. All mutants had much lower basal activity than the corresponding activity of the wild type VLCAD. Their apparent Michaelis constant (Km) was 7-14-fold higher than the Km of the wild type protein whereas their apparent Vmax was either 15-50% lower or double as compared to the wild type VLCAD. Importantly, S-nitrosylation of mutated VLCAD lowered the apparent Km by a factor ranging from 7 to 14 fold (on average 11 fold decrease). In addition, S-nitrosylation of mutated VLCAD slightly reduced the Vmax. Overall, the data indicates that S-nitrosylation of VLCAD on cysteine 237 corrects the enzymatic deficiency of mutated VLCAD by lowering the Km. In other words, treatment with S-nitroso-N-acetylcysteine (SNAC) increased VLCAD enzymatic activity reflected by normal values of apparent $K_M$, and restored mFAO capacity in VLCAD deficient cells.

TABLE 2

Kinetics parameters of mutant and wild-type VLCAD.

| | NAC | | | SNO-NAC | | |
| --- | --- | --- | --- | --- | --- | --- |
| | Vmax (µU/mg) | $K_M$ (mM) | mFAO (nmol/mg/h) | Vmax (µU/mg) | $K_M$ (mM) | mFAO (nmol/mg/h) |
| Patient 1 (G185S/G295E) | 125 | 1.14 | 0.6 | 83 | 0.09 | 3.9 |
| Patient 2 (P91Q/G193R) | 155 | 1.52 | 0.4 | 119 | 0.11 | 4.7 |
| Patient 3 (P89S/A536fsX550) | 239 | 1.07 | 0.8 | 160 | 0.17 | 4.9 |
| Patient 4 (N122D/N122D) | 604 | 1.85 | 0.5 | 343 | 0.16 | 4.1 |
| Healthy donor | 269 | 0.13 | 2.6 | 259 | 0.08 | 3.9 |

Furthermore, a mercury resin assisted capture (MRC) technology followed by mass spectrometry based detection was used to confirm that SNO-NAC treatment results in the S-nitrosylation of cysteine 237. Specifically, the MS/MS spectrum revealed the presence of the double charged peptide TSAVPSC$_{237}$GKYYTLNGSK (SEQ ID NO: 4), corresponding to sequence 231-247 of human VLCAD, only in cell homogenates from SNAC-treated VLCAD-deficient cells. Notably, no other modification of VLCAD was detected. These data demonstrate that S-nitrosylation of VLCAD increased catalytic efficiency in the presence of other mutations and show that protein S-nitrosylation corrects VCLAD enzymatic deficiency.

Example 3

Figure 7A:
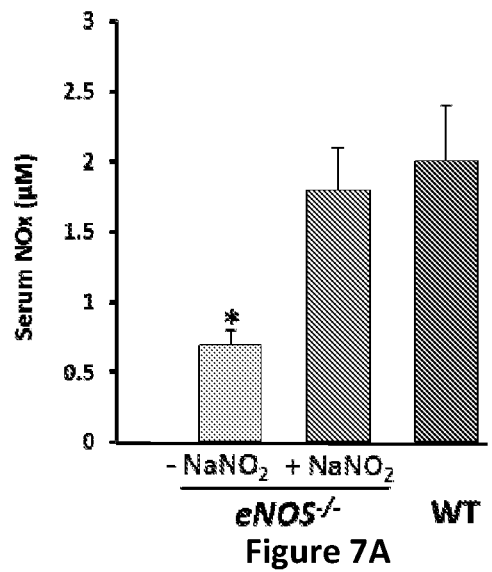
FIGS. 7A-7D show the effects of nitrite administration on eNOS$^{-/-}$ mice.
Figure 7C:
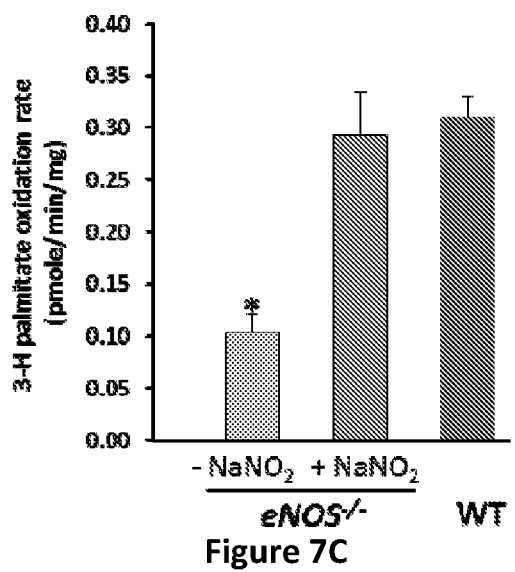
Figure 7B:
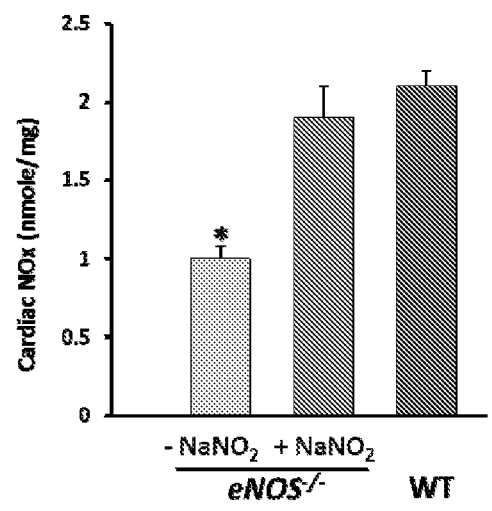
Figure 7D:
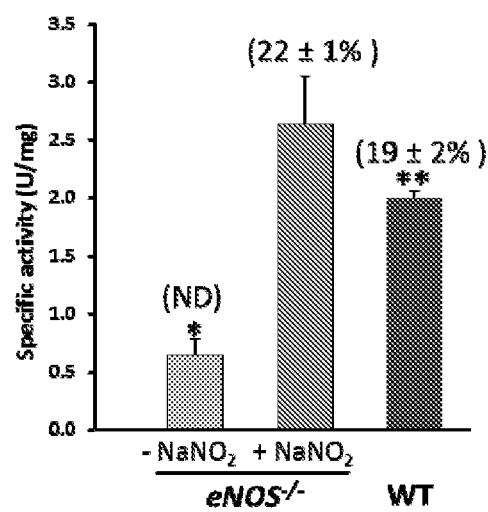

Experiments were conducted in mice (eNOS$^{-/-}$) which have reduced serum and cardiac levels of bioactive nitrogen species as compared to wild type mice (FIGS. 7A and 7B). eNOS$^{-/-}$ mice exhibit lower mFAO rate in the cardiac muscle as compared to wild type mice (FIG. 7C). This finding is consistent with previous studies reporting reduced mFAO capacity in the liver and skeletal muscle of eNOS$^{-/-}$ mice and demonstrates that eNOS-derived NO systemically impacts mFAO capacity. Cardiac VLCAD protein abundance was the same in eNOS null and wild type mice (4.3±0.1 vs 4.2±0.3 µg/mg respectively, N=3 for both genotypes). However, specific activity was over three-fold lower in the eNOS$^{-/-}$ as compared to wild type mice (FIG. 7D). It was determined that 19±2% of VLCAD molecules are endogenously S-nitrosylated in wild type heart. These data provide evidence that eNOS-derived NO is required for endogenous S-nitrosylation of cardiac VLCAD and in the absence of S-nitrosylation the enzymatic activity is significantly lower indicating a positive regulatory effect of S-nitrosylation.

Sodium nitrite at concentration of 0.1 mM was administrated into the drinking water to eNOS$^{-/-}$ mice for 10 days. NaNO$_2$-treated mice exhibited elevated levels of serum and cardiac nitrogen oxides (FIGS. 7A and 7B) as compared to the untreated eNOS$^{-/-}$ mice and similar levels as compared to wild type mice (FIGS. 7A and 7B). Cardiac mFAO rate was normalized to control mice (FIG. 7C). VLCAD protein abundance did not differ as compared to untreated eNOS$^{-/-}$ and wild type mice (4.1±0.3 µg/mg, N=3). Importantly, a greater than 4-fold increase of VLCAD specific activity was documented in NaNO$_2$-treated mice as compared to untreated controls (FIG. 7D). The increased enzymatic activity was associated with the restoration of VLCAD S-nitrosylation. Collectively, the data indicate that: (i) VLCAD is endogenously S-nitrosylated in wild type heart and this post translational modification regulates enzymatic activity; (ii) sodium nitrite effectively restores VLCAD S-nitrosylation in vivo; and (iii) S-nitrosylation of VLCAD increases enzymatic activity in vivo and contributes towards the normalization of mFAO capacity in the cardiac muscle.

Example 4

Figure 9A:
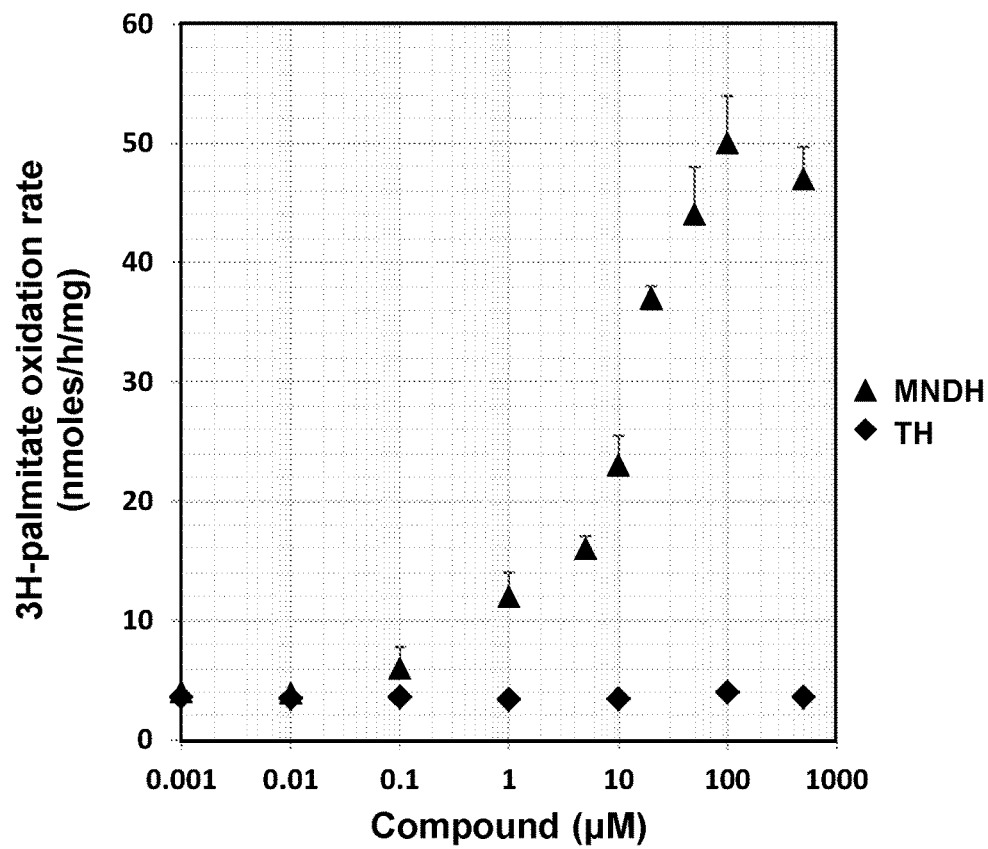
FIG. 9A provides a graph of palmitate oxidation rate in the presence of 2-mononitrate-1,3-diheptanoin (MNDH) or triheptanoin (TH).
Figure 9B:
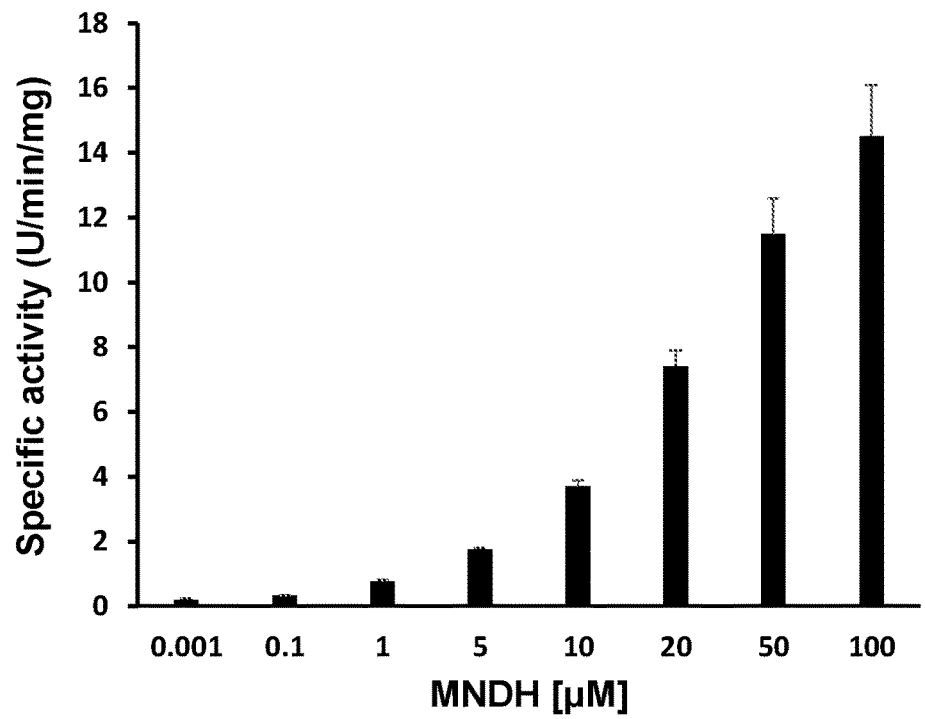
FIG. 9B provides a graph of VLCAD specific activity in the presence of MNDH.

Non-disease control human fibroblasts were exposed for 4 hours to 2-mononitrate-1,3-diheptanoin (MNDH) or triheptanoin (TH), which is used as a control. FIG. 9A shows the concentration-dependent increase in palmitate oxidation in the presence of MNDH, but not TH control. FIG. 9B shows the concentration-dependent increase in VLCAD specific activity in the presence of MNDH.

The toxicity of MNDH and TH was also studied. Notably, the number of viable cells is the same as untreated controls 24 hour after exposure for 4, 8, or 12 hours to 3-mononitrate-1,3-diheptanoin (MNDH) or triheptanoin (TH). Furthermore, protein levels were the same after 24 hour exposure to MNDH or TH as compared to controls. Thus, MNDH and TH were not toxic.

Figure 10A:
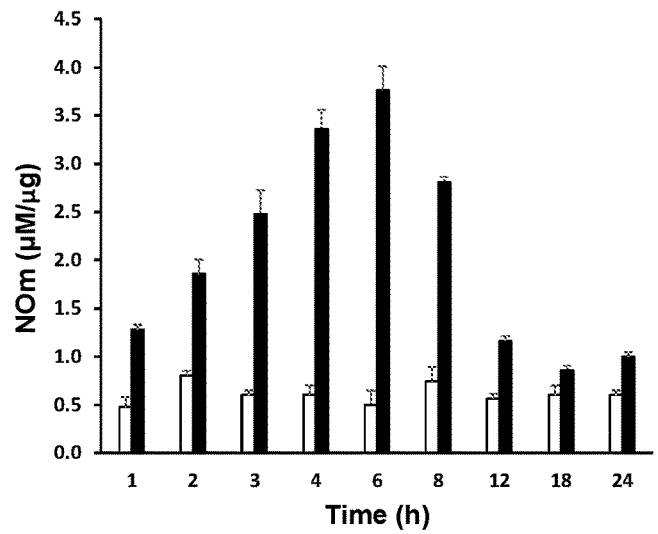
FIG. 10A provides a graph of the total levels of nitric oxide metabolites (NOm) after exposure to MNDH (black bars) or TH (white bars).
Figure 10B:
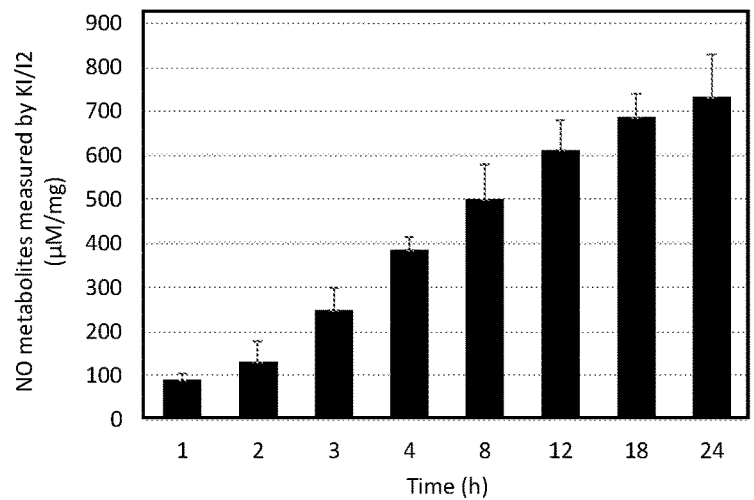
FIG. 10B provides a graph of nitrite levels over time.
Figure 10C:
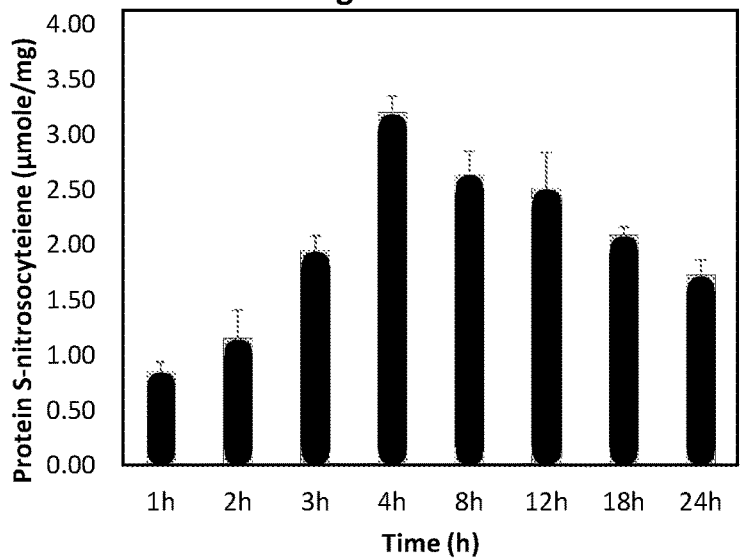
FIG. 10C provides a graph of total protein S-nitrosocysteine over time after exposure to MNDH.

The metabolism of MNDH in human fibroblasts was also studied. FIG. 10A shows that the total levels of nitric oxide metabolites (NOm) increased for the first 6 hours of exposure to 100 µM MNDH and levels declined thereafter. TH does not increase levels of NO metabolites. FIG. 10B shows that levels of nitrite in the cells increase over time after exposure to MNDH. Therefore, the decline in total NO metabolites may reflect metabolism of MNDH. FIG. 10C shows that the levels of total protein S-nitrosocysteine also increased after exposure to MNDH. Levels declined with time, thereby indicating protein S-nitrosylation turnover. The levels of S-nitrosylated proteins in TH-treated cells were lower than 10 pmole/mg protein.

Figure 11A:
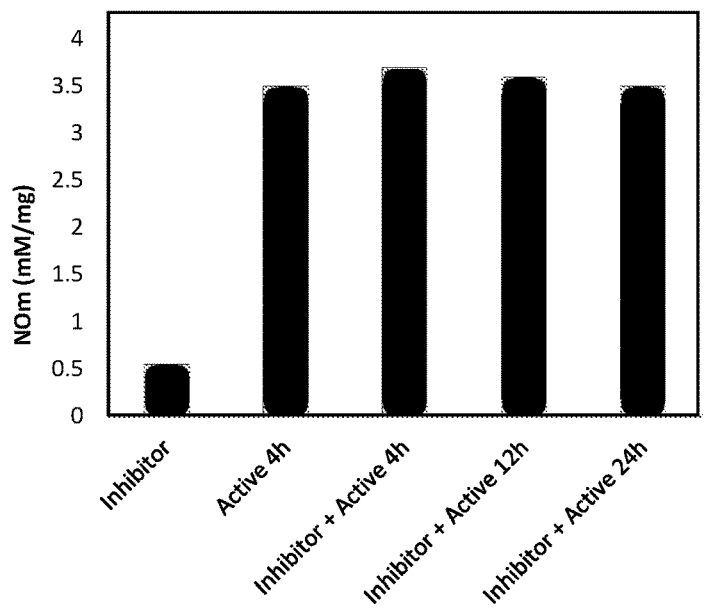
FIG. 11A provides a graph of nitric oxide metabolites (NOm) after exposure to MNDH (active) and/or daidzin (inhibitor).
Figure 11B:
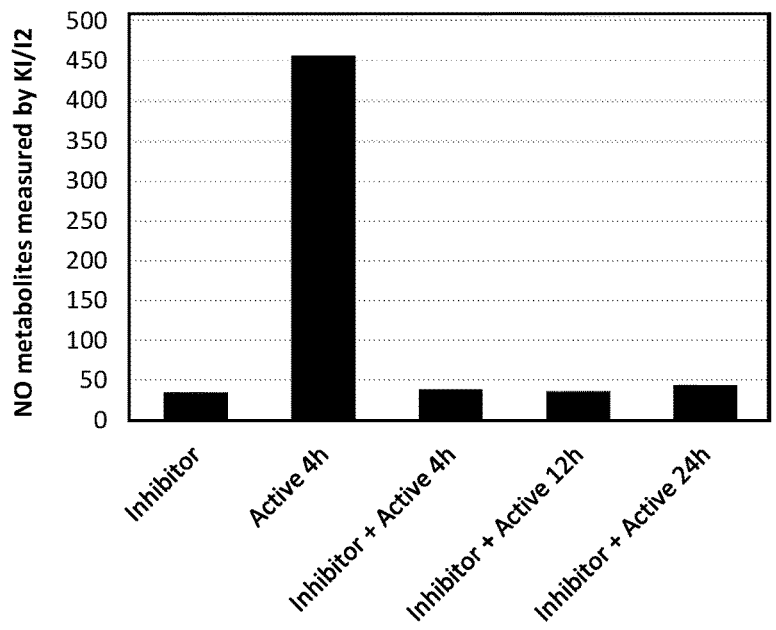
FIG. 11B provides a graph of nitrite levels over time after exposure to MNDH (active) and/or daidzin (inhibitor).

FIG. 11A shows that the inhibition of mitochondrial aldehyde dehydrogenase 2 by pre-treatment for 1 hour with daidzin prevents the metabolism of MNDH. The inhibitor was present during the incubation with the active compound. FIG. 11B shows the MNDH generated nitrite as measured by the KI/I2 reduction and shows that the pre-treatment for 1 hour with daidzin prevents the metabolism of MNDH.

Figure 11C:
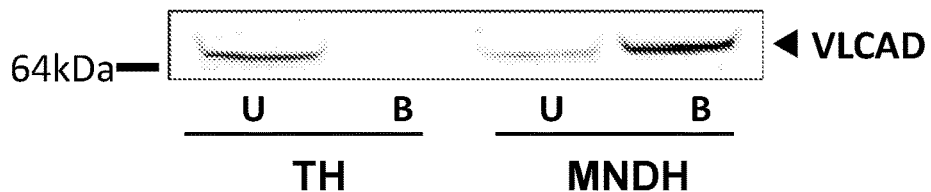
FIG. 11C provides an image of a blot of S-nitrosylated VLCAD pull-down assays. Bound (B) and unbound (U) samples are shown. Cells were treated with MNDH or TH (control).

S-nitrosylation of VLCAD by MNDH was also confirmed. FIG. 11C shows the selective capture of S-nitrosylated VLCAD after exposing cells to TH of MNDH. Significantly, FIG. 11C shows that nearly 50% of VLCAD molecules were modified in the presence of MNDH, but not TH. S-nitrosylation at cysteine 237 was confirmed by peptide digestion and MS/MS analysis.

Figure 12A:
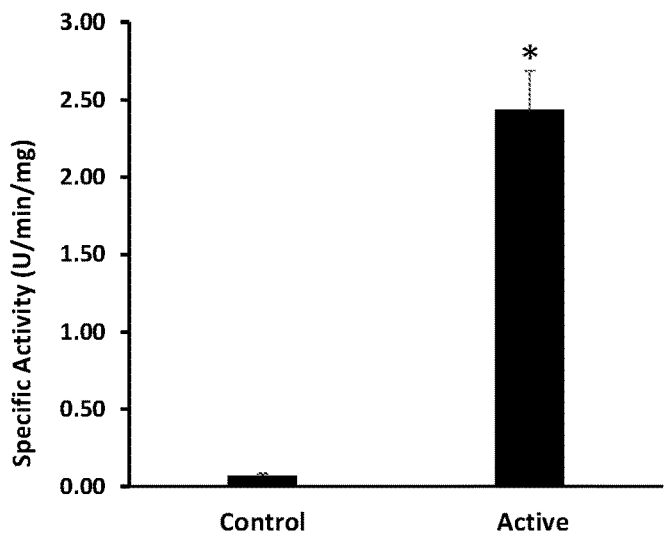
FIG. 12A provides a graph of the VLCAD specific activity in fibroblasts with a mutant VLCAD (G185S/G294E) exposed to TH (control) or MNDH (active). *p<0.001, N=3.
Figure 12B:
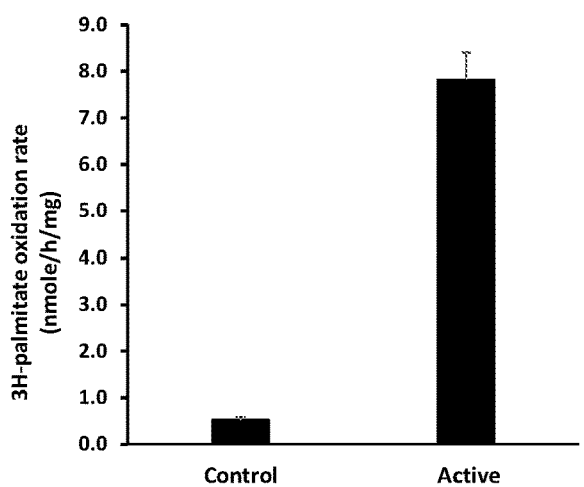
FIG. 12B provides a graph of the palmitate oxidation rate in fibroblasts with a mutant VLCAD (G185S/G294E) exposed to TH (control) or MNDH (active). *p<0.001, N=3.
Figure 12C:
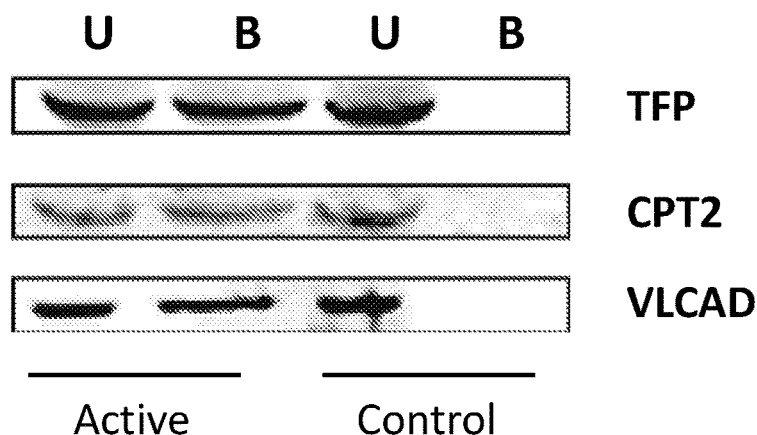
FIG. 12C provides images of blots showing the S-nitrosylation of VLCAD, trifunctional proteins (TFP), and carnitine palmitotransferase-2 (CPT2). U: unbound; B: bound. VLCAD protein levels=0.49±0.08 μg/mg.

Fibroblasts with the G185S/G294E VLCAD mutation were treated for 4 hours with 100 µM of TH (control) or MNDH (active) conjugated to BSA. As seen in FIG. 12A, exposure to MNDH—but not TH—increased mutant VLCAD specific activity by 40-fold. Further, as seen in FIG. 12B, exposure to MNDH—but not TH—increased mFAO rate by 16 fold. As seen in FIG. 12C, exposure to MNDH—but not TH—resulted in the S-nitrosylation of VLCAD, trifunctional proteins (TFP), and carnitine palmitotransferase-2 (CPT2).

Figure 13A:
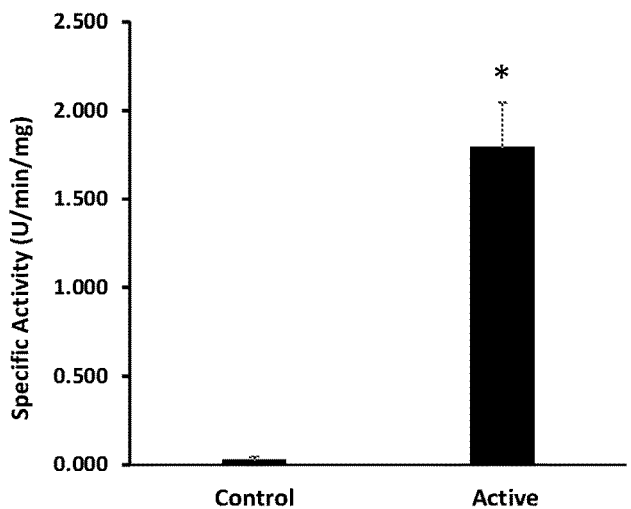
FIG. 13A provides a graph of the VLCAD specific activity in fibroblasts with a mutant VLCAD (P91Q/G193R) exposed to TH (control) or MNDH (active). *p<0.001, N=3.
Figure 13B:
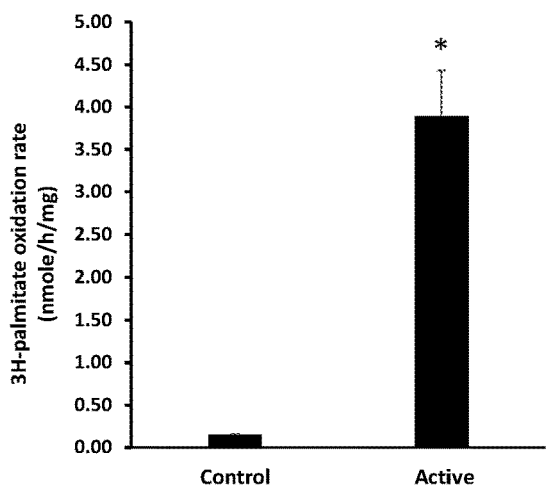
FIG. 13B provides a graph of the palmitate oxidation rate in fibroblasts with a mutant VLCAD (P91Q/G193R) exposed to TH (control) or MNDH (active). *p<0.001, N=3.
Figure 13C:
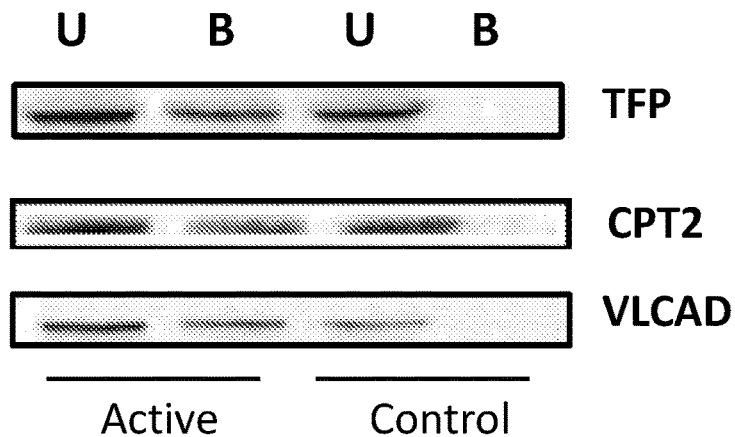
FIG. 13C provides images of blots showing the S-nitrosylation of VLCAD, trifunctional proteins (TFP), and carnitine palmitotransferase-2 (CPT2). U: unbound; B: bound. VLCAD protein levels=0.70±0.1 µg/mg.

Fibroblasts with the P91Q/G193R VLCAD mutation were treated for 4 hours with 100 µM of TH (control) or MNDH (active) conjugated to BSA. As seen in FIG. 13A, exposure to MNDH—but not TH—increased mutant VLCAD specific activity by 75-fold. Further, as seen in FIG. 13B, exposure to MNDH—but not TH—increased mFAO rate by 28 fold. As seen in FIG. 13C, exposure to MNDH—but not TH—resulted in the S-nitrosylation of VLCAD, trifunctional proteins (TFP), and carnitine palmitotransferase-2 (CPT2).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating a fatty acid oxidation disorder in a subject, said method comprising administering at least one S-nitrosylating agent to said subject,
wherein said S-nitrosylating agent is a triglyceride wherein one or two fatty acid chains have been replaced with nitrate, nitroso, or nitro.

2. The method of claim 1, wherein said fatty acid oxidation disorder is selected from the group consisting of very long-chain acyl-coenzyme A dehydrogenase deficiency (VLCADD), long-chain 3-hydroxyacyl-coenzyme A dehydrogenase deficiency (LCHADD), medium-chain acyl-CoA dehydrogenase deficiency (MCADD), short chain acyl-CoA dehydrogenase deficiency (SCADD), medium/short chain L-3-hydroxyacyl-CoA dehydrogenase deficiency (M/SCHADD), multiple acyl-CoA dehydrogenase deficiency (MADD), mitochondrial trifunctional protein deficiency, short chain 3-ketoacyl-CoA thiolase deficiency (SKATD), medium chain 3-ketoacyl-CoA thiolase deficiency (MCKATD), 2,4-dienoyl-CoA reductase deficiency, and glutaric acidemia type II (GA-II).

3. The method of claim 2, wherein said fatty acid oxidation disorder is VLCADD.

4. The method of claim 1, wherein said S-nitrosylating agent is a triglyceride wherein one or two fatty acid chains have been replaced with nitrate.

5. The method of claim 1, wherein the fatty acids of the triglyceride comprise at least 7 carbons.

6. The method of claim 5, wherein the fatty acids of the triglyceride are 7 to 11 carbons in length.

7. The method of claim 1, wherein said S-nitrosylating agent is selected from the group consisting of 1,3-dinitrate-2-heptanoin; 1,2-dinitrate-3-heptanoin; and 2,3-dinitrate-1-heptanoin.

8. The method of claim 1, further comprising the administration of S-nitroso-N-acetyl-cysteine (SNO-NAC).

9. The method of claim 1, further comprising the administration of at least one other therapeutic agent for the treatment of the fatty acid oxidation disorder.

10. The method of claim 9, wherein said other therapeutic agent is triheptanoin or bezafibrate.

11. The method of claim 1, further comprising diagnosing a fatty acid oxidation disorder in said subject prior to administration of said S-nitrosylating agent.

12. The method of claim 11, wherein said diagnosis comprises:
   a) obtaining a biological sample from said subject;
   b) determining the enzymatic activity of the very long-chain acyl-coenzyme A dehydrogenase (VLCAD) in said sample; and
   c) comparing the amount of VLCAD enzymatic activity determined in step b) to the amount of VLCAD enzymatic activity in a corresponding biological sample from a healthy subject, wherein a decrease in the VLCAD enzymatic activity in the biological sample from the subject compared to the healthy subject is indicative of a fatty acid oxidation disorder in said subject.

13. The method of claim 11, wherein the diagnosis comprises determining the presence of a mutation in a the very long-chain acyl-coenzyme A dehydrogenase (VLCAD) encoding nucleic acid molecule in a biological sample obtained from said subject, wherein the presence of a mutation in the VLCAD encoding nucleic acid molecule is indicative of a fatty acid oxidation disorder in said subject.

14. The method of claim 1, wherein said S-nitrosylating agent is a triglyceride wherein two fatty acid chains have been replaced with nitrate, nitroso, or nitro.

* * * * *